(12) United States Patent
Kim et al.

(10) Patent No.: US 7,604,919 B2
(45) Date of Patent: Oct. 20, 2009

(54) MONOMER, POLYMER AND COMPOSITION FOR PHOTORESIST

(75) Inventors: Deog-Bae Kim, Seoul (KR); Jung-Youl Lee, Anyang-si (KR); Geun-Jong Yu, Jeonju-si (KR); Sang-Jung Kim, Incheon (KR); Jae-Woo Lee, Bucheon-si (KR); Jae-Hyun Kim, Seoul (KR)

(73) Assignee: Dongjin Semichem Co., Ltd., Incheon (KR)

( * ) Notice: Subject to any disclaimer, the term of this patent is extended or adjusted under 35 U.S.C. 154(b) by 24 days.

(21) Appl. No.: 11/852,664

(22) Filed: Sep. 10, 2007

(65) Prior Publication Data

US 2008/0070161 A1    Mar. 20, 2008

(30) Foreign Application Priority Data

Sep. 11, 2006    (KR) ..................... 10-2006-0087655

(51) Int. Cl.
| | |
|---|---|
| *G03F 7/039* | (2006.01) |
| *G03F 7/038* | (2006.01) |
| *G03F 7/20* | (2006.01) |
| *G03F 7/30* | (2006.01) |
| *G03F 7/38* | (2006.01) |

(52) U.S. Cl. ..................... 430/270.1; 430/905; 430/910; 430/330; 430/325; 430/326; 526/287; 526/228; 564/254

(58) Field of Classification Search ....................... None
See application file for complete search history.

(56) References Cited

U.S. PATENT DOCUMENTS

2004/0033440 A1*   2/2004   Maeda et al. ............ 430/270.1
2008/0102402 A1*   5/2008   Lee et al. ................. 430/270.1

* cited by examiner

*Primary Examiner*—Sin J. Lee
(74) *Attorney, Agent, or Firm*—Birch, Stewart, Kolasch & Birch, LLP

(57) ABSTRACT

The photoresist monomer including an oxime group, a polymer thereof and a photoresist composition containing the same are disclosed. The photoresist monomer is represented by following Formula.

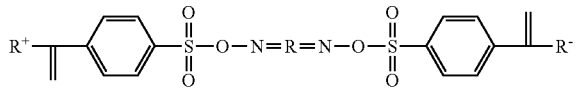

In Formula, R* is independently a hydrogen or a methyl group, and R is a substituted or unsubstituted $C_1$~$C_{25}$ alkyl group with or without an ether group, or a substituted or unsubstituted $C_4$~$C_{25}$ hydrocarbon group including an aryl group, a heteroaryl group, a cycloalkyl group or a multicycloalkyl group with or without an ether group, a ketone group or a sulfur.

9 Claims, No Drawings

MONOMER, POLYMER AND COMPOSITION FOR PHOTORESIST

This application claims the priority benefit of Korean Patent Application No. 10-2006-0087655 filed on Sep. 11, 2006. All disclosure of the Korean Patent application is incorporated herein by reference.

FIELD OF THE INVENTION

This invention relates to a monomer, a polymer and a composition for photoresist, and more particularly, to a photoresist monomer, a polymer thereof and a photoresist composition containing at least two oxime groups.

BACKGROUNDS OF THE INVENTION

Recently, as the integration degree and the precision of semiconductor devices increase, the formation of ultra-fine photoresist patterns, which have a half pitch of less than 90 nm, is required in the photolithography process for producing the semiconductor devices. Thus, in the photolithography process, the wavelength of an exposure light is reduced to less than 193 nm, and various technologies for optimizing the pattern forming process have been being developed. In order to produce the fine photoresist patterns, it is also necessary to develop photosensitive materials having a low LER(Line Edge Roughness), a low PEB(Post Exposure Baking) temperature sensitivity, and a good dry etching resistance.

In order to improve the resolution and the process margin in forming the photoresist pattern, and to produce a more fine photoresist pattern, the photosensitive photoresist polymer should have a low activation energy in the deprotection reaction of a protecting group, in which the protecting group is adhered to the side chain of the photoresist polymer for inhibiting the dissolution of the polymer against a basic solution, or the photosensitive polymer should be materials having a low PEB(Post Exposure Baking) temperature sensitivity, that is, materials being less affected by an acid. In summary, a fine photoresist pattern can be obtained by using a polymer which is less affected by an acid and whose main chain is decomposed by the exposure light.

In the meantime, a monomer and a (meth)acrylate polymer thereof, which can be used with KrF(254 nm), ArF(193 nm), $F_2$(157 nm) or EUVL(13.5 nm) exposure light source, and have at least two oxime groups which can be deprotected by the exposure light, have not been known or disclosed.

SUMMARY OF THE INVENTION

Therefore, it is an object of the present invention to provide a photoresist monomer, a polymer thereof and a photoresist composition including the same, which can improve the resolution and the process margin of a photolithography process.

It is other object of the present invention to provide a photoresist monomer, a polymer thereof and a photoresist composition including the same, which have a low PEB (Post Exposure Baking) temperature sensitivity, and produce fine photoresist patterns.

It is another object of the present invention to provide a photoresist monomer, a polymer thereof and a photoresist composition including the same, which can improve the focus depth margin and the line edge roughness of photoresist patterns.

It is still another object of the present invention to provide a method of forming a photoresist pattern using the photoresist composition.

To accomplish these objects, the present invention provides a monomer having at least two oxime groups and represented by the following Formula 1.

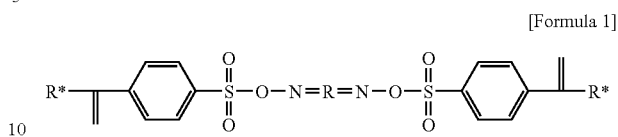

[Formula 1]

In Formula 1, R* is independently a hydrogen or a methyl group, and R is a substituted or unsubstituted $C_1$~$C_{25}$ alkyl group with or without an ether group, or a substituted or unsubstituted $C_4$~$C_{25}$ hydrocarbon group including an aryl group, a heteroaryl group, a cycloalkyl group or a multicycloalkyl group with or without an ether group, a ketone group or a sulfur.

Also, the present invention provides a photoresist polymer which includes a repeating unit represented by the following Formula 2 and whose main chain can be decomposed by ultraviolet rays as well as an acid catalyst.

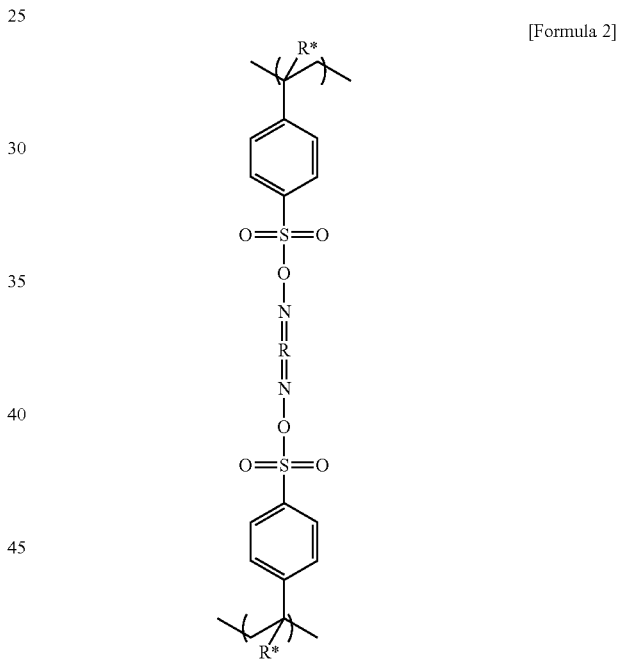

[Formula 2]

In Formula 2, R* is independently a hydrogen or a methyl group, and R is a substituted or unsubstituted $C_1$~$C_{25}$ alkyl group with or without an ether group, or a substituted or unsubstituted $C_4$~$C_{25}$ hydrocarbon group including an aryl group, a heteroaryl group, a cycloalkyl group or a multicycloalkyl group with or without an ether group, a ketone group or a sulfur.

DETAILED DESCRIPTION OF THE INVENTION

A more complete appreciation of the invention, and many of the attendant advantages thereof, will be better appreciated by reference to the following detailed description.

The photoresist monomer having an oxime group according to the present invention can be represented by the following Formula 1.

[Formula 1]

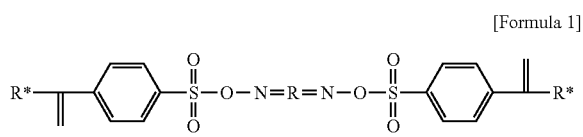

In Formula 1, R* is independently a hydrogen or a methyl group, and R is a substituted or unsubstituted $C_1$~$C_{25}$ alkyl group with or without an ether group, or a substituted or unsubstituted $C_4$~$C_{25}$ hydrocarbon group including an aryl group, a heteroaryl group, a cycloalkyl group or a multicycloalkyl group with or without an ether group, a ketone group or a sulfur. Examples of R include =CH—CH=, =CH—CH$_2$—CH=,

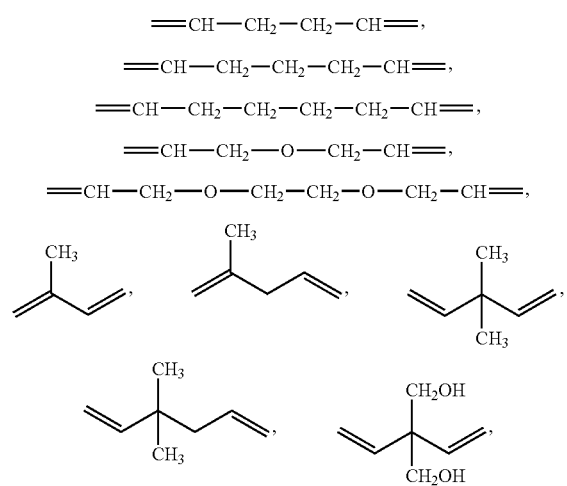

-continued

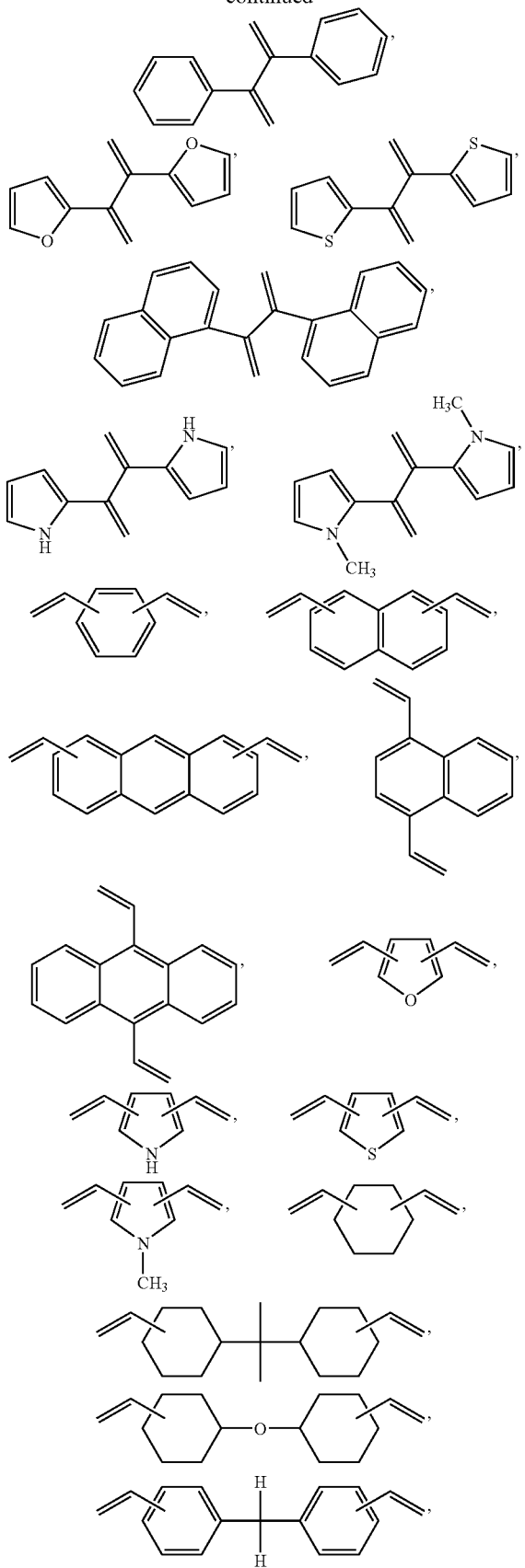

Among them, preferable examples of R include [structures shown].

In the photosensitive monomer of Formula 1 according to the present invention, the deprotection reaction can be carried out by an acid catalyst, but the deprotection reaction can also be carried out by ultraviolet rays without an acid catalyst, which is due to a photosensitive functional group, the oxime group. The deprotection reaction without the acid catalyst reduces the molecular weight of a polymer and changes the physical properties of the polymer. Thus, after a light exposure process, the compatibility of the polymer and a developer can be enhanced. Accordingly, in the developing process, fine photoresist patterns can be more easily produced and the line edge roughness of the photoresist patterns can be improved in comparison with the conventional polymer.

The photoresist polymer having an oxime group according to the present invention includes a repeating unit represented by the following Formula 2.

[Formula 2]

In Formula 2, R* and R are as defined in Formula 1. In the photoresist polymer of the present invention, the amount of the repeating unit of Formula 2 is 1~99 mole %, preferably 1~50 mole % in the upper polymer chain and in the lower polymer chain, respectively. The remaining repeating unit composing the photoresist polymer of the present invention can be one or more conventional repeating units, which compose a conventional photoresist polymer. For example, the photoresist polymer according to the present invention can be represented by the following Formula 3 or Formula 4.

[Formula 3]

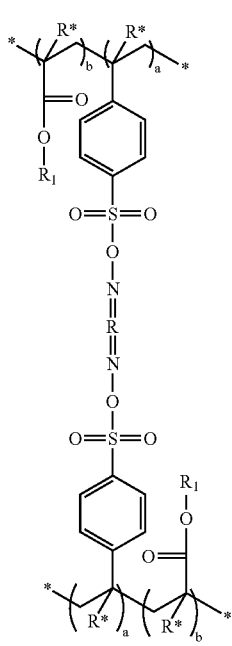

In Formula 3, R* and R are as defined in Formula 1. $R_1$ is a protection group which is sensitive to an acid, and independently is a $C_1$~$C_{25}$ alkyl group or cycloalkyl group with or without an ether group or an ester group. a and b independently represent mole % of repeating units constituting the upper polymer chain and the lower polymer chain, and are 1~99 mole % and 1~99 mole %, respectively. Preferably, a:b is 1~50 mole %: 50~99 mole % in each polymer chain.

The acid sensitive protection group $R_1$ can be separated (decomposed) by an acid, and the solubility of the polymer in an alkali developing solution depends on the kind of the acid sensitive protection group. As the acid sensitive protection group, any functional group capable of performing the above-mentioned function can be used. Exemplary protection group includes, but is not limited to, t-butyl, 3-hydroxy tetrahydrofuran, tetrahydro-3-furanmethanol, tetrahydrofurfuryl alcohol, 1-methoxypropyl, 1-methoxy-1-methylethyl, 1-ethoxypropyl, 1-ethoxy-1-methylethyl, 1-methoxyethyl, 1-ethoxyethyl, t-buthoxyethyl, 1-isobutoxyethyl and 2-methoxy ethanol or adamantyl group.

As shown in following Formula 4, the photoresist polymer according to the present invention may further include another repeating unit for controlling the physical property of the polymer, besides the acid sensitive protection group $R_1$.

[Formula 4]

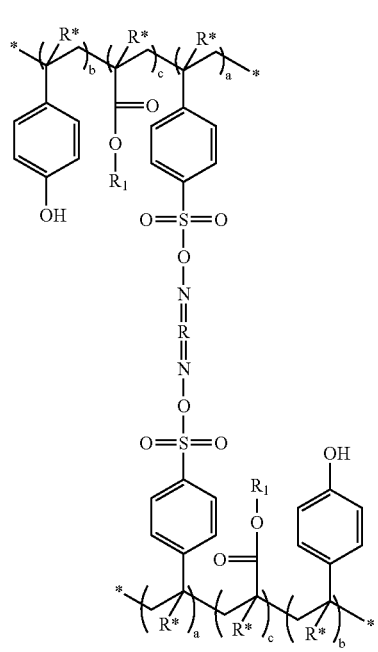

In Formula 4, R* and R are as defined in Formula 1, and $R_1$ is as defined in Formula 3. a, b and c independently represent mole % of repeating units constituting the upper polymer chain and the lower polymer chain, and are 1~98 mole %, 1~98 mole % and 1~98 mole %, respectively. Preferably, a:b:c is 1~50 mole % 20~50 mole % 15~50 mole %.

The more specific example of Formula 2 can be represented by the following Formula 5 or Formula 6.

[Formula 5]

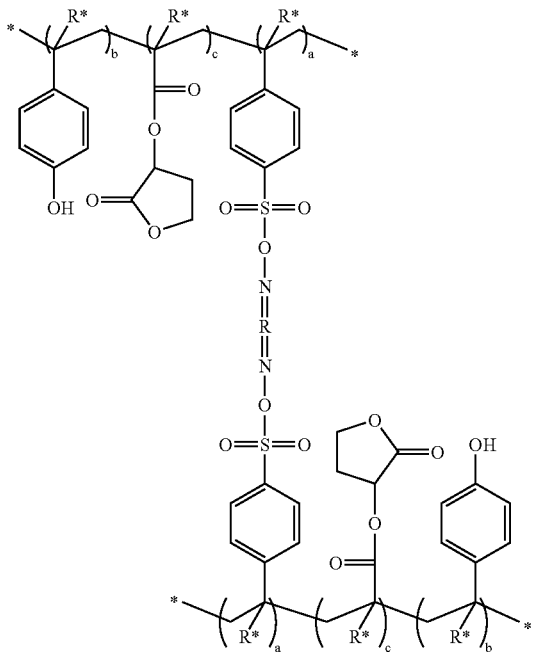

In Formula 5, R* and R are as defined in Formula 1, and a, b and c are as defined in Formula 4.

The photosensitive polymer of the present invention may further include other auxiliary monomers, such as, cycloolefin monomer (for example, maleic anhydride), another conventional monomer for forming a photosensitive polymer, cross-linking monomer, and so on, besides the monomer having the acid sensitive protection group $R_1$. Preferably, the amount of the auxiliary monomers is 0~5 mole % with respect to the total repeating unit. The photosensitive polymer according to the present invention may be a block copolymer or a random copolymer. The weight-average molecular weight (Mw) of the photosensitive polymer is preferably 3,000 to 20,000 and more preferably 3,000 to 15,000. The polydispersity thereof is preferably 1.0 to 5.0 and more preferably 1.0 to 2.2. If the weight-average molecular weight and the polydispersity of the photosensitive polymer deviate from the above mentioned ranges, the physical property of the photoresist layer can be degraded, the formation of photoresist layer is difficult and contrast of the photoresist patterns can be deteriorated.

The photosensitive monomer of the present invention can be prepared by a) substituting ketone groups with oxime groups by quantitatively reacting a compound having at least two ketone groups and hydroxylamine hydrochloride ($NH_2OH$ HCl), and b) by reacting the oxime group with a sulfonyl compound at room temperature and atmospheric pressure in the presence of a base such as triethylamine, pyridine etc.

The photosensitive polymer of the present invention can be prepared by a conventional polymerization reaction using the monomer of Formula 1 and other conventional monomer. In the polymerization, conventional polymerization initiator can

[Formula 6]

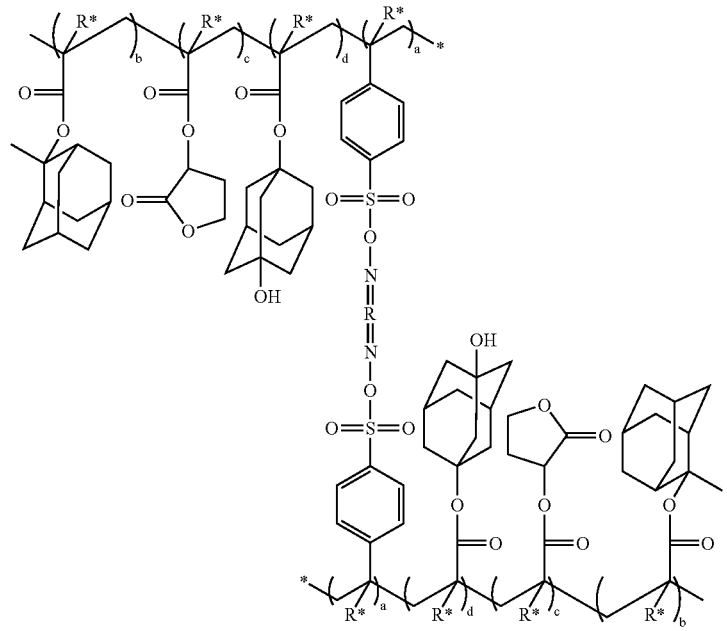

In Formula 6, R* and R are as defined in Formula 1. a, b, c and d independently represent mole % of repeating units constituting the upper polymer chain and the lower polymer chain, and are 1~97 mole %, 1~97 mole %, 1~97 mole % and 1~97 mole %, respectively. Preferably, a:b:c:d is 1~50 mole % : 20~40 mole %: 20~40 mole % 10~40 mole %.

be widely used, and the exemplary initiator includes, but is not limited to, azobis(isobutyronitrile) (AIBN).

The photoresist composition according to the present invention can be prepared by mixing the photosensitive polymer containing the monomer represented by Formula 1, a photo-acid generator for generating an acid, and an organic solvent, and, if necessary, various additives. The preferable concentration of the solid components in the photoresist composition is 1~30 weight % with respect to the total photoresist composition. The photoresist composition can be used after filtering with 0.2 μm filter.

As the photo-acid generator, any conventional photo-acid generator, which can generate an acid when exposed to light, can be used. The non-limiting examples of the photo-acid generator include organic sulfonic acid, onium salt or the mixtures thereof. The preferable amount of the photo-acid generator is 0.1 to 20 weight parts with respect to 100 weight parts of the photoresist polymer. If the amount of the photo-acid generator is less than 0.1 weight parts, the light sensitivity of the photoresist composition may decrease. If the amount of the photo-acid generator is more than 20 weight parts, the profile of the resist patterns may be deteriorated because the photo-acid generator absorbs a lot of ultraviolet rays and a large quantity of acid is produced from the photo-acid generator.

The conventional various organic solvents for a photoresist composition can be used as the organic solvent of the photoresist composition of the present invention. Exemplary organic solvent include, but are not limited to, ethyleneglycol monomethylethyl, ethyleneglycol monoethylether, ethyleneglycol monomethylether, diethyleneglycol monoethylether, propyleneglycol monomethyletheracetate(PGMEA), toluene, xylene, methylethylketone, cyclohexanone, ethyl 2-hydroxy propionate, ethyl 2-hydroxy-2-methyl propionate, ethoxyethyl acetate, hydroxyethyl acetate, methyl 2-hydroxy-3-methylbutanoate, methyl 3-methoxy-2-methylpropionate, ethyl 3-ethoxy propionate, ethyl 3-methoxy-2-methyl propionate, ethyl acetate, butyl acetate, and the mixtures thereof. The preferable amount of the organic solvent is 300~5000 weight parts with respect to the total photoresist polymer 100 weight parts.

In addition, the photoresist composition of the present invention may further include an organic base. The preferable amount of the organic base is 0.01~10 weight %. Exemplary organic base includes, but not limited to, triethylamine, triisobutylamine, triisooctylamine, diethanolamine, triethanolamine and the mixtures thereof.

In order to form a photoresist pattern with the photoresist composition according to the present invention, the following conventional photolithography process can be carried out. First, the photoresist composition is applied or coated on a substrate such as silicon wafer, an aluminum substrate, and so on, for example, with a spin coater to form a photoresist layer. The photoresist layer is exposed to a light of a predetermined pattern. After the exposure, if necessary, the photoresist pattern is thermally treated (heated), which is called as PEB (Post Exposure Bake), and is developed to form the photoresist pattern. As the developing solution for the developing process, an alkali aqueous solution including an alkali compound such as sodium hydroxide, potassium hydroxide, sodium carbonate, tetramethylammonium hydroxide (TMAH) of the concentration of 0.1 to 10 weight % can be used. If necessary, the developing solution may further include water-soluble organic solvent such as methanol, ethanol and a surfactant of a proper amount. After developing, the cleaning process of the substrate can be carried out, in which the substrate is washed with purified water.

Hereinafter, the preferable examples are provided for better understanding of the present invention. However, the present invention is not limited to the following examples.

[Manufacturing Example] Preparation of 4-vinyl-benzosulfonyl chloride 4-vinyl-benzosulfonyl chloride was prepared as shown in the following Reaction 1. First, 103 g (0.50 mol) of 4-stylenesulfonyl sodium salt and 1000 g of THF (tetrahydrofuran) were added into a 2 L flask and mixed, and the temperature was maintained at 0° C. Thereafter, 72 g (0.2 mol) of $POCl_3$ was slowly dropped to the reaction mixture. And then, the reaction mixture was reacted for 12 hours. After completion of the reaction, the reactant was filtered under reduced pressure and washed with 1 L of saturated aqueous sodium carbonate solution for 3 times. Thereafter, the reactant was dried to obtain 91.9 g of 4-vinyl-benzosulfonyl chloride (Yield: 91%).

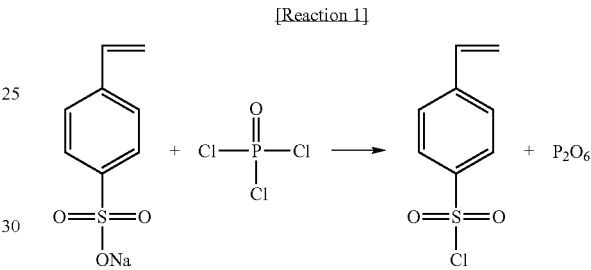

[Reaction 1]

EXAMPLE 1-1

Preparation of Compound of Formula 1a 9.8 g (0.10 mol) of cyclopentane-1,3-dione and 150 g of methanol were added into a 500 mL flask and mixed, and the temperature was maintained at 0° C. Thereafter, 15.3 g (0.22 mol) of hydroxylamine hydrochloride was slowly dropped to the mixture, and the reaction was carried out for 12 hours. After completion of the reaction, the reactant was filtered under reduced pressure and washed with 300 mL of distilled water for 3 times. Thereafter the reactant was dried to obtain 13.5 g of compound of Formula 1a (Yield: 56%). $^1$H-NMR ($CDCl_3$, internal standard): δ(ppm) 5.89(OH, 2H), 1.42($CH_2$, 2H), 1.33($CH_2$, 4H)

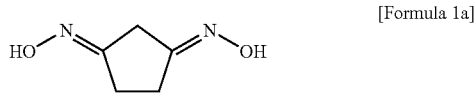

[Formula 1a]

EXAMPLE 1-2

Preparation of Compound of Formula 1b

Except for using 11.2 g (0.1 mol) of cyclohexane-1,4-dione instead of 9.8 g of cyclopentane-1,3-dione, the reaction was carried out in the same manner as described in Example 1-1 to obtain 11.2 g of compound of following Formula 1b(Yield: 79%). 1H-NMR ($CDCl_3$, internal standard): δ(ppm) 5.94(OH, 2H), 1.61($CH_2$, 8H)

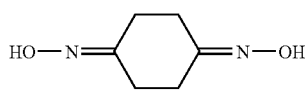
[Formula 1b]

EXAMPLE 1-3

Preparation of Compound of Formula 1c

Except for using 16.6 g (0.1 mol) of 1,5-dimethylbicyclo[3,3,0]octane-3,7-dione instead of 9.8 g of cyclopentane-1,3-dione, the reaction was carried out in the same manner as described in Example 1-1 to obtain 16.6 g of compound of following Formula 1c(Yield: 85%). $^1$H-NMR (CDCl$_3$, internal standard): δ(ppm) 5.85(OH, 2H), 1.64(CH, 8H), 1.09 (CH$_3$, 6H)

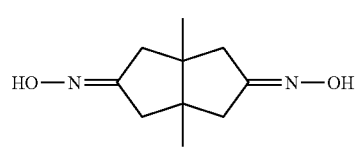
[Formula 1c]

EXAMPLE 1-4

Preparation of Compound of Formula 1d

Except for using 15.2 g (0.1 mol) of 7,7-dimethyl-bicyclo[2.2.1]heptane-2,3-dione instead of 9.8 g of cyclopentane-1,3-dione, the reaction was carried out in the same manner as described in Example 1-1 to obtain 14.0 g of compound of the following Formula 1d(Yield: 77%). $^1$H-NMR (CDCl$_3$, internal standard): δ(ppm) 5.88(OH, 2H), 1.76(CH, 2H), 1.41 (CH$_2$, 4H), 1.11(CH$_3$, 6H)

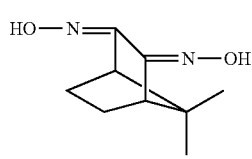
[Formula 1d]

EXAMPLE 1-5

Preparation of Compound of Formula 1e

Except for using 16.4 g (0.1 mol) of adamantane-2,6-dione instead of 9.8 g of cyclopentane-1,3-dione, the reaction was carried out in the same manner as described in Example 1-1 to obtain 13.8 g of compound of following Formula 1e(Yield: 71%). $^1$H-NMR (CDCl$_3$, internal standard): δ(ppm) 5.94(OH, 2H), 1.78(CH, 4H), 1.51(CH$_2$, 8H)

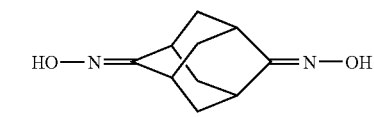
[Formula 1e]

EXAMPLE 1-6

Preparation of Compound of Formula 1f

Except for using 23.6 g (0.1 mol) of 2,2'-bis-4,4'-carbonylcyclohexyl propane dione instead of 9.8 g of cyclopentane-1,3-dione, the reaction was carried out in the same manner as described in Example 1-1 to obtain 25.0 g of compound of following Formula 1f(Yield: 94%). $^1$H-NMR (CDCl$_3$, internal standard): δ(ppm) 5.88(OH, 2H), 1.61(CH$_2$, 8H), 1.56 (CH, 2H), 1.33(CH$_2$, 8H), 1.09(CH$_3$, 6H)

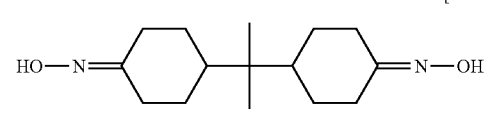
[Formula 1f]

EXAMPLE 1-7

Preparation of Compound of Following Formula 1g

Except for using 19.4 g (0.1 mol) of 2,2'-bis-4,4'-carbonylcyclohexyl dione instead of 9.8 g of cyclopentane-1,3-dione, the reaction was carried out in the same manner as described in Example 1-1 to obtain 21.3 g of compound of following Formula 1g(Yield: 95%). $^1$H-NMR (CDCl$_3$, internal standard): δ(ppm) 5.90(OH, 2H), 1.58(CH$_2$, 8H), 1.51 (CH, 2H), 1.31(CH$_2$, 8H)

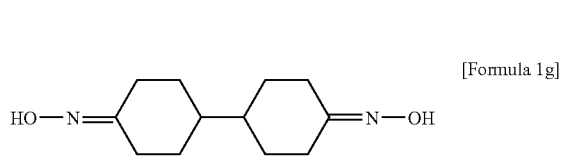
[Formula 1g]

EXAMPLE 1-8

Preparation of Compound of Formula 1h

Except for using 21.0 g (0.1 mol) of 1,2-bezene-2nyl-ethane-1,2-dione instead of 9.8 g of cyclopentane-1,3-dione, the reaction was carried out in the same manner as described in Example 1-1 to obtain 13.5 g of compound of following Formula 1h(Yield: 56%). $^1$H-NMR (CDCl$_3$, internal standard): δ(ppm) 8.59(OH, 2H), 7.62(CH, 4H), 7.32(CH, 6H)

[Formula 1h]

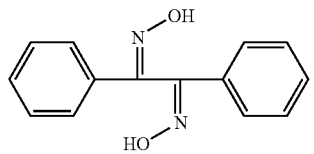

EXAMPLE 1-9

Preparation of Compound of Formula 1i

Except for using 19.0 g (0.1 mol) of 1,2-difuran-2nyl-ethane-1,2-dione instead of 9.8 g of cyclopentane-1,3-dione, the reaction was carried out in the same manner as described in Example 1-1 to obtain 7.0 g of compound of following Formula 1i(Yield: 32%). $^1$H-NMR (CDCl$_3$, internal standard): δ(ppm) 8.61(OH, 2H), 7.35(CH, 2H), 6.23(CH, 2H), 6.15(CH, 2H)

[Formula 1i]

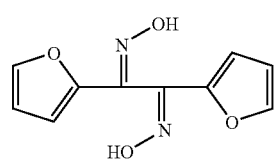

EXAMPLE 1-10

Preparation of Compound of Formula 1j

Except for using 31.0 g (0.1 mol) of 1,2-dinaphthalene-1-nyl-ethane-1,2-dione instead of 9.8 g of cyclopentane-1,3-dione, the reaction was carried out in the same manner as described in Example 1-1 to obtain 16.3 g of compound of Formula 1j(Yield: 48%). $^1$H-NMR (CDCl$_3$, internal standard): δ(ppm) 8.59(OH, 2H), 7.99(CH, 2H), 7.85(CH, 2H), 7.63(CH, 4H), 7.55(CH, 2H), 7.33(CH, 4H)

[Formula 1j]

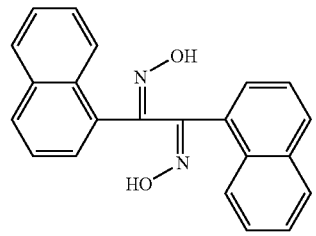

EXAMPLE 1-11

Preparation of Compound of Formula 1k

Except for using 18.3 g (0.1 mol) of 1,2-bis-(1H-pyrrole-2-nyl)-ethane-1,2-dione instead of 9.8 g of cyclopentane-1, 3-dione, the reaction was carried out in the same manner as described in Example 1-1 to obtain 12.9 g of compound of following Formula 1k(Yield: 59%). $^1$H-NMR (CDCl$_3$, internal standard): δ(ppm) 8.52(OH, 2H), 6.56(CH, 2H), 6.61 (CH, 2H), 6.54(CH, 2H), 5.23(NH, 2H)

[Formula 1k]

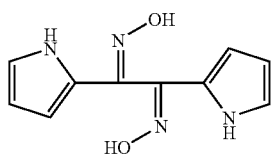

EXAMPLE 1-12

Preparation of Compound of Formula 1l

Except for using 13.4 g (0.1 mol) of benzene-1,4-dicarboxaldehyde instead of 9.8 g of cyclopentane-1,3-dione, the reaction was carried out in the same manner as described in Example 1-1 to obtain 15.6 g of compound of following Formula 1l(Yield: 95%). $^1$H-NMR (CDCl$_3$, internal standard): δ(ppm) 8.24(OH, 2H), 8.12(CH, 2H), 7.94(CH, 4H)

[Formula 1l]

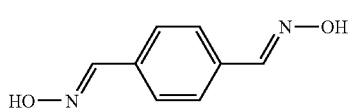

EXAMPLE 1-13

Preparation of Compound of Formula 1m

Except for using 18.4 g (0.1 mol) of naphthalene-1,4-dicarboxaldehyde instead of 9.8 g of cyclopentane-1,3-dione, the reaction was carried out in the same manner as described in Example 1-1 to obtain 20.4 g of compound of following Formula 1m(Yield: 95%). $^1$H-NMR(CDCl$_3$, internal standard): δ(ppm) 8.21(OH, 2H), 8.24(CH, 4H), 7.59(CH, 2H), 7.29(CH, 2H)

[Formula 1m]

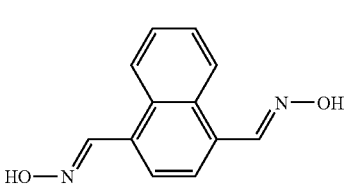

EXAMPLE 1-14

Preparation of Compound of Formula 1n

Except for using 23.4 g (0.1 mol) of antracene-9,10-dicarboxaldehyde instead of 9.8 g of cyclopentane-1,3-dione, the reaction was carried out in the same manner as described in Example 1-1 to obtain 24.6 g of compound of following Formula 1n(Yield: 91%). $^1$H-NMR (CDCl$_3$, internal standard): δ(ppm) 8.61(OH, 2H), 8.21(CH, 2H), 7.88(CH, 4H), 7.33(CH, 4H)

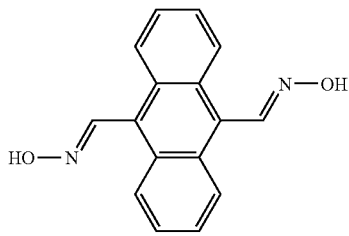

[Formula 1n]

EXAMPLE 2-1

Preparation of Compound of Formula 2a 6.4 g (0.05 mol) of cyclopentane-1,3-dione-dioxime prepared in Example 1-1 and 100 g of pyridine were added into a 500 mL flask and mixed, and the temperature of the mixture was maintained at 0° C. 30.3 g (0.15 mol) of 4-vinyl-benzosulfonyl chloride prepared in Manufacturing example was slowly dropped to the mixture. Then reactor was heated to room temperature and the reaction was performed for 12 hours. After completion of the reaction, 500 mL of diethylether was added to the reactant and the unreacted compounds were removed by using saturated aqueous sodium carbonate solution. After separating the water layer, remaining water was removed by using anhydrous magnesium sulfate, and distillation under reduced pressure was performed to obtain 19.6 g of monomer of following Formula 2a(Yield: 85%). $^1$H-NMR (CDCl$_3$, internal standard): δ(ppm) 7.89(CH, 4H), 7.52(CH, 4H), 6.58(CH, 2H), 5.54(CH$_2$, 2H), 5.14(CH$_2$, 2H), 1.42(CH$_2$, 2H), 1.33(CH$_2$, 4H)

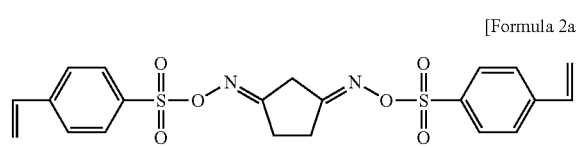

[Formula 2a]

EXAMPLE 2-2

Preparation of Compound of Formula 2b

Except for using 7.1 g (0.05 mol) of cyclohexane-1,4-dione-dioxime instead of 6.4 g of cyclopentane-1,3-dione-dioxime, the reaction was carried out in the same manner as described in Example 2-1 to obtain 18.5 g of compound of following Formula 2b(Yield: 78%). $^1$H-NMR (CDCl$_3$, internal standard): δ(ppm) 7.87(CH, 4H), 7.48(CH, 4H), 6.60(CH, 2H), 5.56(CH$_2$, 2H), 5.15(CH$_2$, 2H), 1.64(CH$_2$, 8H)

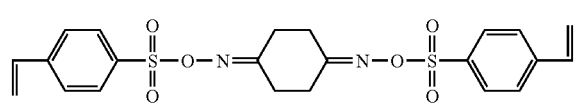

[Formula 2b]

EXAMPLE 2-3

Preparation of Compound of Formula 2c

Except for using 9.8 g (0.05 mol) of 1,5-dimethyl-bicyclo[3,3,0]octane-3,7-dione-dioxime instead of 6.4 g of cyclopentane-1,3-dione-dioxime, the reaction was carried out in the same manner as described in Example 2-1 to obtain 22.2 g of compound of following Formula 2c(Yield: 84%). $^1$H-NMR(CDCl$_3$, internal standard): δ(ppm) 7.85(CH, 4H), 7.50(CH, 4H), 6.55(CH, 2H), 5.53(CH$_2$, 2H), 5.12(CH$_2$, 2H), 1.62(CH$_2$, 8H), 1.09(CH$_3$, 6H)

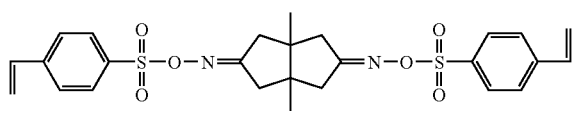

[Formula 2c]

EXAMPLE 2-4

Preparation of Compound of Formula 2d

Except for using 9.1 g (0.05 mol) of 7,7-dimethyl-bicyclo[2,2,1]heptane-2,3-dione-dioxime instead of 6.4 g of cyclopentane-1,3-dione-dioxime, the reaction was carried out in the same manner as described in Example 2-1 to obtain 19.8 g of compound of following Formula 2d(Yield: 77%). $^1$H-NMR (CDCl$_3$, internal standard): δ(ppm) 7.87(CH, 4H), 7.51(CH, 4H), 6.58(CH, 2H), 5.48(CH$_2$, 2H), 5.21(CH$_2$, 2H), 1.68(CH, 2H), 1.42(CH$_2$, 4H), 1.09(CH$_3$, 6H)

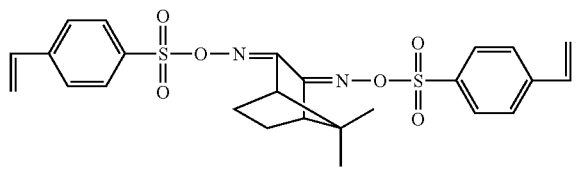

[Formula 2d]

EXAMPLE 2-5

Preparation of Compound of Formula 2e

Except for using 9.7 g (0.05 mol) of adamantane-2,6-dione-dioxime instead of 6.4 g of cyclopentane-1,3-dione-dioxime, the reaction was carried out in the same manner as described in Example 2-1 to obtain 19.5 g of compound of following Formula 2e(Yield: 74%). $^1$H-NMR (CDCl$_3$, internal standard): δ(ppm) 7.87(CH, 4H), 7.53(CH, 4H), 6.55(CH, 2H), 5.49(CH$_2$, 2H), 5.16(CH$_2$, 2H), 1.72(CH, 4H), 1.49(CH$_2$, 8H)

[Formula 2e]

EXAMPLE 2-6

Preparation of Compound of Formula 2f

Except for using 13.3 g (0.05 mol) of 2,2'-bis-4,4'-carbonylcyclohexyl propane-dione dioxime instead of 6.4 g of cyclopentane-1,3-dione-dioxime, the reaction was carried out in the same manner as described in Example 2-1 to obtain 25.7 g of compound of following Formula 2f(Yield: 86%). $^1$H-NMR (CDCl$_3$, internal standard): δ(ppm) 7.86(CH, 4H), 7.53(CH, 4H), 6.59(CH, 2H), 5.49(CH$_2$, 2H), 5.14(CH$_2$, 2H), 1.64(CH$_2$, 8H), 1.52(CH, 2H), 1.32(CH$_2$, 8H), 1.07(CH$_3$, 6H)

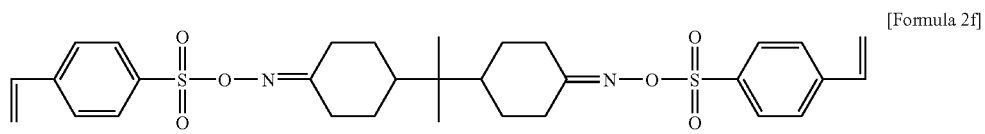

[Formula 2f]

EXAMPLE 2-7

Preparation of compound of Formula 2g

Except for using 11.21 g (0.05 mol) of 2,2'-bis-4,4'-carbonyl cyclohexyl-dione-dioxime instead of 6.4 g of cyclopentane-1,3-dione-dioxime, the reaction was carried out in the same manner as described in Example 2-1 to obtain 23.6 g of compound of following Formula 2g(Yield: 85%). $^1$H-NMR (CDCl$_3$, internal standard): δ(ppm) 7.82(CH, 4H), 7.48(CH, 4H), 6.49(CH, 2H), 5.54(CH$_2$, 2H), 5.18(CH$_2$, 2H), 1.60(CH$_2$, 8H), 1.49(CH, 2H), 1.30(CH$_2$, 8H)

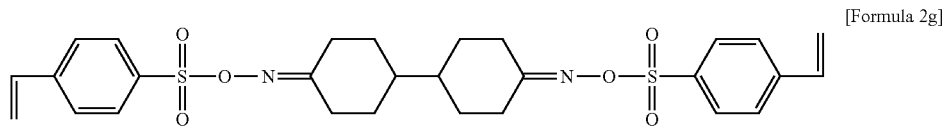

[Formula 2g]

EXAMPLE 2-8

Preparation of Compound of Formula 2h

Except for using 12.0 g (0.05 mol) of 1,2-benzen-2nyl-ethane-1,2-dione-dioxime instead of 6.4 g of cyclopentane-1,3-dione-dioxime, the reaction was carried out in the same manner as described in Example 2-1 to obtain 23.2 g of compound of following Formula 2h(Yield: 81%). $^1$H-NMR (CDCl$_3$, internal standard): δ(ppm) 7.86(CH, 4H), 7.63(CH, 4H), 7.52(CH, 4H), 7.36(CH, 6H), 6.58(CH, 2H), 5.48(CH$_2$, 2H), 5.21(CH$_2$, 2H)

[Formula 2h]

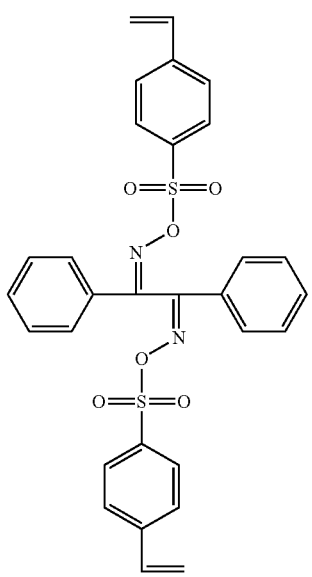

EXAMPLE 2-9

Preparation of Compound of Formula 2i

Except for using 11.0 g (0.05 mol) of 1,2-difuran-2nyl-ethane-1,2-dione-dioxime instead of 6.4 g of cyclopentane-1,3-dione-dioxime, the reaction was carried out in the same manner as described in Example 2-1 to obtain 18.8 g of compound of following Formula 2i(Yield: 68%). $^1$H-NMR (CDCl$_3$, internal standard): δ(ppm) 7.83(CH, 4H), 7.55(CH, 4H), 7.38(CH, 2H), 6.42(CH, 2H), 6.12(CH, 2H), 6.01(CH, 2H), 5.50 (CH$_2$, 2H), 5.15(CH$_2$, 2H)

[Formula 2i]

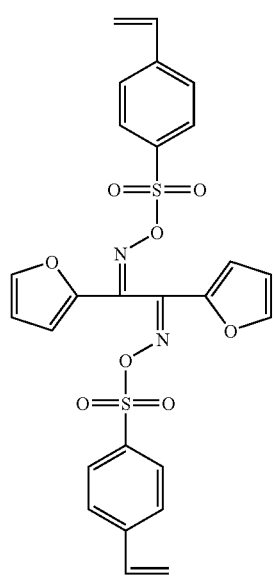

EXAMPLE 2-10

Preparation of Compound of Formula 2j

Except for using 17.0 g (0.05 mol) of 1,2-dinaphthalene-1-nyl-ethane-1,2-dione-dioxime instead of 6.4 g of cyclopentane-1,3-dione-dioxime, the reaction was carried out in the same manner as described in Example 2-1 to obtain 26.2 g of compound of following Formula 2j(Yield: 78%). $^1$H-NMR (CDCl$_3$, internal standard): δ(ppm)) 7.90(CH, 4H), 7.64(CH, 4H), 7.50(CH, 8H), 7.35(CH, 6H), 6.49(CH, 2H), 5.54(CH$_2$, 2H), 5.21(CH$_2$, 2H)

[Formula 2j]

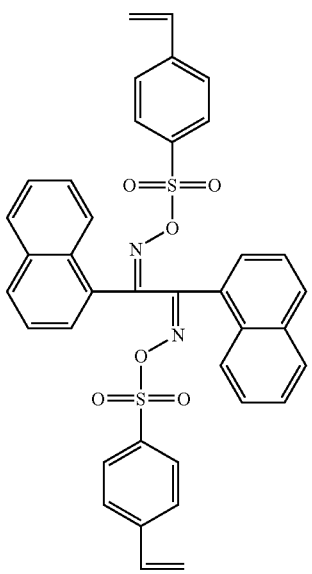

EXAMPLE 2-11

Preparation of Compound of Formula 2k

Except for using 10.9 g (0.05 mol) of 1,2-bis-(1H-pyrrole-2-nyl)-ethane-1,2-dione-dioxime instead of 6.4 g of cyclopentane-1,3-dione-dioxime, the reaction was carried out in the same manner as described in Example 2-1 to obtain 24.2 g of compound of following Formula 2k(Yield: 88%). $^1$H-NMR (CDCl$_3$, internal standard): δ(ppm) 7.84(CH, 4H), 7.49(CH, 4H), 6.58(CH, 2H), 6.40(CH, 2H), 6.22(CH, 4H), 5.54(CH$_2$, 2H), 5.32(CH$_2$, 2H), 5.24(NH, 2H), 5.16(CH$_2$, 2H)

[Formula 2k]

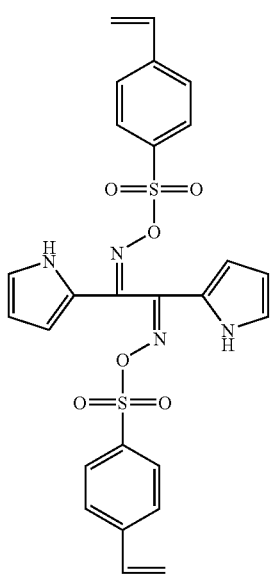

EXAMPLE 2-12

Preparation of Compound of Formula 2l

Except for using 8.2 g (0.05 mol) of benzen-1,4-dicarboxaldehyde-dioxime instead of 6.4 of cyclopentane-1,3-dione-dioxime, the reaction was carried out in the same manner as described in Example 2-1 to obtain 17.9 g of compound of following Formula 2l(Yield: 72%). $^1$H-NMR (CDCl$_3$, internal standard): δ(ppm) 8.14(CH, 2H), 7.88(CH, 8H), 7.51(CH, 4H), 6.45(CH, 2H), 5.48(CH$_2$, 2H), 5.20(CH$_2$, 2H)

[Formula 2l]

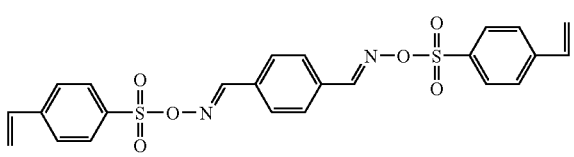

EXAMPLE 2-13

Preparation of Compound of Formula 2m

Except for using 10.7 g (0.05 mol) of naphthalene-1,4-dicarboxaldehyde-dioxime instead of 6.4 g of cyclopentane-1,3-dione-dioxime, the reaction was carried out in the same manner as described in Example 2-1 to obtain 17.7 g of compound of following Formula 2m(Yield: 65%). $^1$H-NMR (CDCl$_3$, internal standard): δ(ppm) 8.22(CH, 2H), 7.84(CH, 4H), 7.52(CH, 6H), 7.26(CH, 2H), 6.51(CH, 2H), 5.50(CH$_2$, 2H), 5.19(CH$_2$, 2H)

[Formula 2m]

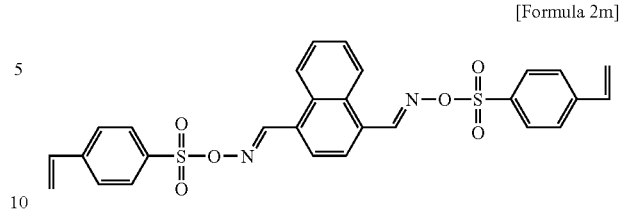

EXAMPLE 2-14

Preparation of Compound of Formula 2n

Except for using 13.2 g (0.05 mol) of antracene-9,10-dicarboxaldehyde-dioxime instead of 6.4 g (0.05 mol) of cyclopentane-1,3-dione-dioxime, the reaction was carried out in the same manner as described in Example 2-1 to obtain 17.3 g of compound of following Formula 2n(Yield: 58%). $^1$H-NMR (CDCl$_3$, internal standard): δ(ppm) 8.23(CH, 2H), 7.85(CH, 8H), 7.54(CH, 4H), 7.26(CH, 4H), 6.48(CH, 2H), 5.46(CH$_2$, 2H), 5.21(CH$_2$, 2H)

[Formula 2n]

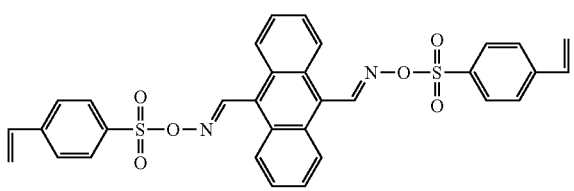

EXAMPLE 3-1

Preparation of Photosensitive Polymer of Formula 3a 200 mL of tetrahydrofuran (THF) was added to a 500 mL 4-neck flask on which a Liebig condenser, a temperature controller and a nitrogen injector were mounted, then nitrogen gas was injected and the reactant was stirred for 30 minutes. 23.00 g of the monomer (Formula 2a) prepared in Example 2-1, 4.25 g of gamma-butyrolacto methacrylate, 4.05 g of 4-acetoxystyrene and 3.13 g of azobis(isobutyronitrile) (AIBN) were added to the reactor and the mixture was stirred for 30 minutes under nitrogen atmosphere at 40° C. Thereafter, the reactor was heated to 70° C. and the polymerization was performed for 24 hours. After the completion of the polymerization, the reactor was cooled to room temperature and the reaction solution was added into 2 L of hexane to obtain a precipitate. Next, the obtained precipitate was filtered, washed with 1 L of hexane for several times and vacuum-dried. After 300 mL of methanol and 50 mL of 30% NH$_4$OH aqueous solution were added to the flask containing the dried polymer, the mixture was slowly stirred at 50° C. to completely dissolve the polymer and further stirred for 30 minutes. The dissolved solution was added into 1.5 L of water to obtain a precipitate. The obtained precipitate was filtered, washed with 2 L of purified water for several times, and vacuum-dried for 2 days to prepare 22.50 g of photosensitive polymer, of following Formula 3a(Yield: 72%). The molecular weight (Mw) and polydispersity (PD) of the prepared polymer were measured with GPC (Gel permeation chromatography), and Mw was 10,650 and PD was 1.78.

[Formula 3a]

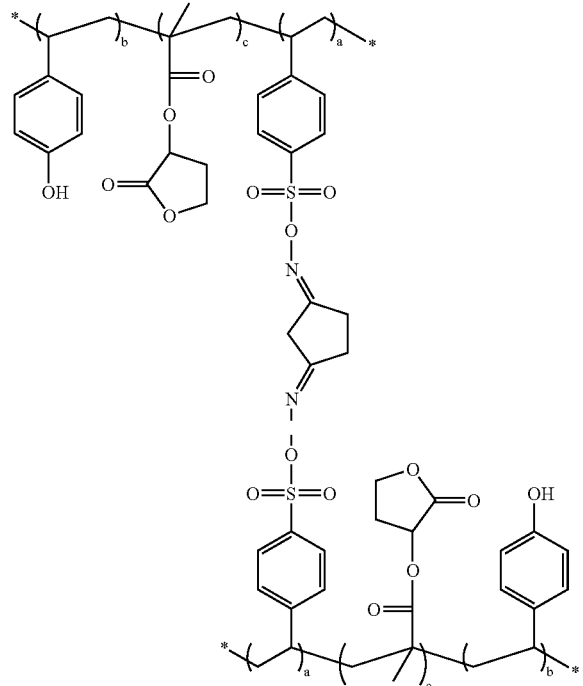

EXAMPLE 3-2

Preparation of Photosensitive Polymer of Formula 3b

Except for using 23.70 g of monomer of Formula 2b instead of 23.00 g of monomer of Formula 2a, the polymerization reaction was carried out in the same manner as described in Example 3-1 to obtain 22.70 g of polymer of following Formula 3b(Yield: 71%). From the GPC analysis of the polymer, Mw was 11,201 and PD was 1.94.

[Formula 3b]

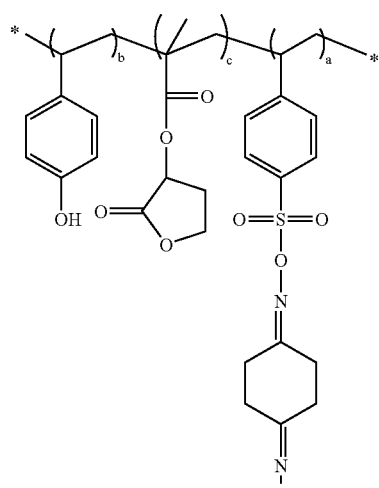

-continued

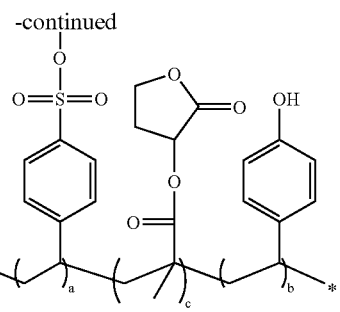

EXAMPLE 3-3

Preparation of Photosensitive Polymer of Formula 3c

Except for using 26.40 g of monomer of Formula 2c instead of 23.00 g of monomer of Formula 2a, the polymerization reaction was carried out in the same manner as described in Example 3-1 to obtain 26.40 g of polymer of following Formula 3c(Yield: 76%). From the GPC analysis of the polymer, Mw was 11,569 and PD was 1.95.

[Formula 3c]

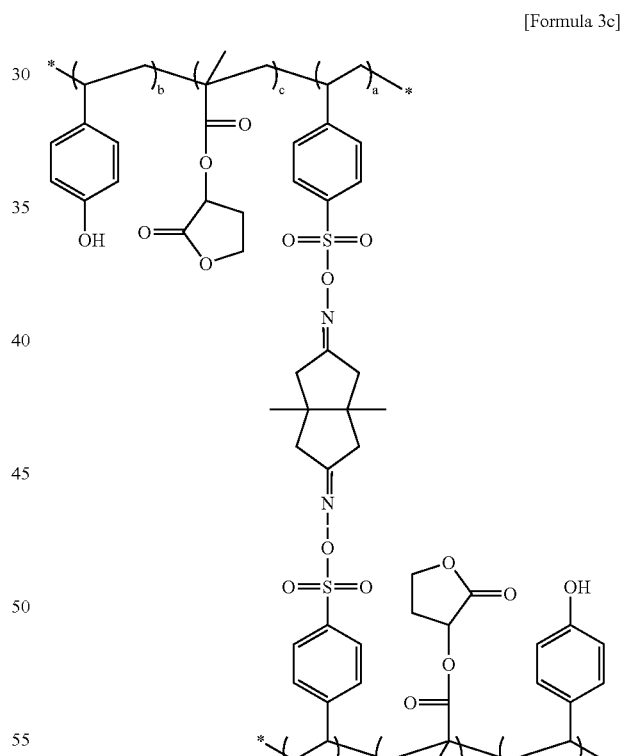

EXAMPLE 3-4

Preparation of Photosensitive Polymer of Formula 3d

Except for using 25.70 g of monomer of Formula 2d instead of 23.00 g of monomer of Formula 2a, the polymerization reaction was carried out in the same manner as described in Example 3-1 to obtain 23.12 g of polymer of following Formula 3d(Yield: 68%). From the GPC analysis of the polymer, Mw was 12,503 and PD was 1.97.

[Formula 3d]

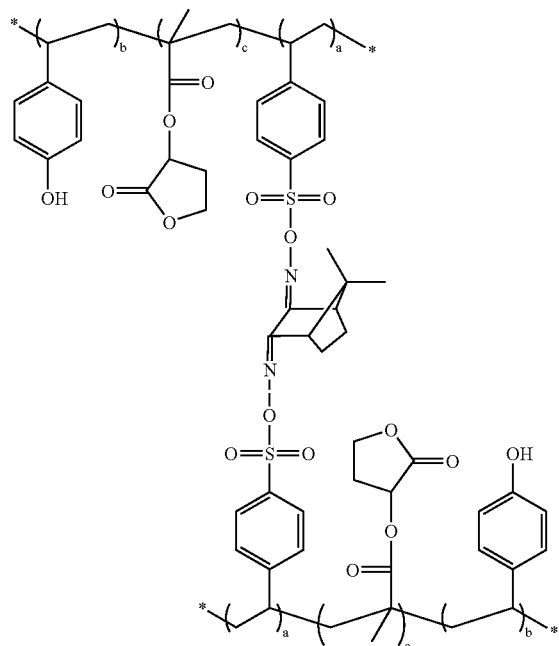

EXAMPLE 3-5

Preparation of Photosensitive Polymer of Formula 3e

Except for using 26.30 g of monomer of Formula 2e instead of 23.00 g of monomer of Formula 2a, the polymerization reaction was carried out in the same manner as described in Example 3-1 to obtain 22.10 g of polymer of following Formula 3e(Yield: 64%). From the GPC analysis of the polymer, Mw was 11,025 and PD was 1.99.

[Formula 3e]

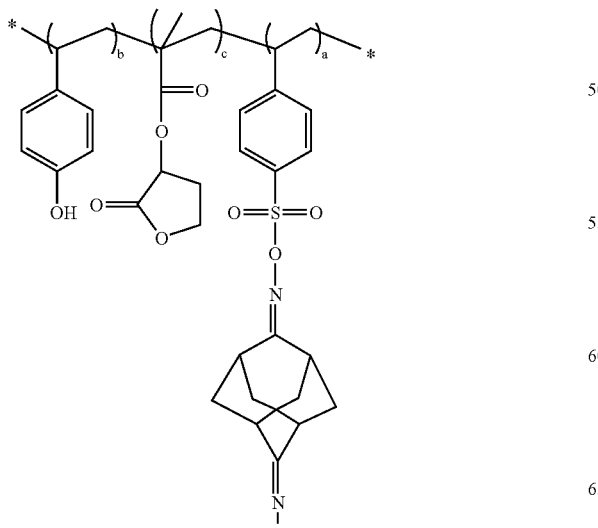

-continued

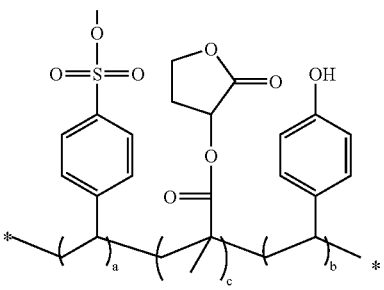

EXAMPLE 3-6

Preparation of Photosensitive Polymer of Formula 3f

Except for using 29.90 g of monomer of Formula 2f instead of 23.00 g of monomer of Formula 2a, the polymerization reaction was carried out in the same manner as described in Example 3-1 to obtain 29.01 g of polymer of following Formula 3f(Yield: 76%). From the GPC analysis of the polymer, Mw was 10,458 and PD was 1.82.

[Formula 3f]

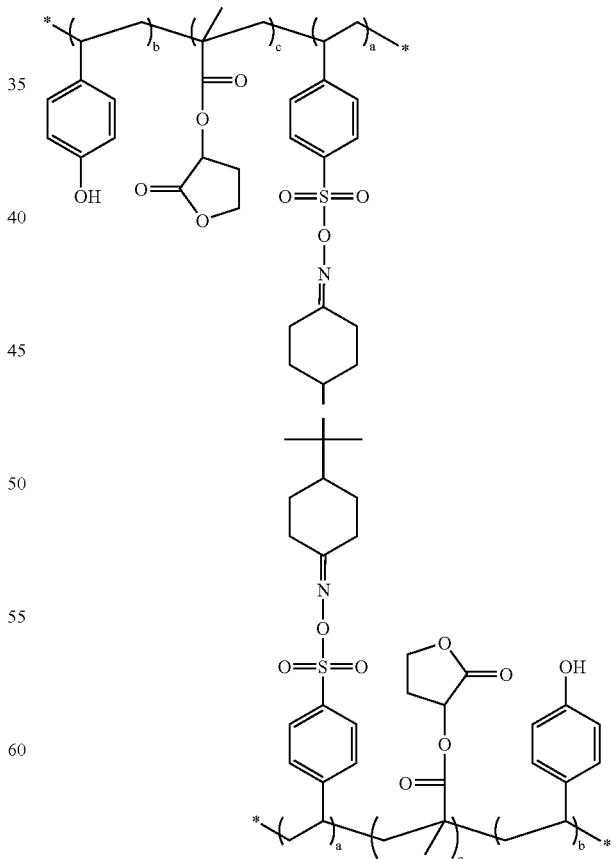

EXAMPLE 3-7

Preparation of Photosensitive Polymer of Formula 3g

Except for using 27.80 g of monomer of Formula 2 g instead of 23.00 g of monomer of Formula 2a, the polymerization reaction was carried out in the same manner as described in Example 3-1 to obtain 25.60 g of polymer of following Formula 3g(Yield: 71%). From the GPC analysis of the polymer, Mw was 9,856 and PD was 1.94.

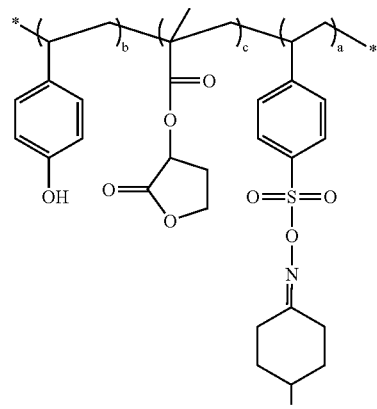

[Formula 3g]

EXAMPLE 3-8

Preparation of Photosensitive Polymer of Formula 3h

Except for using 28.60 g of monomer of by Formula 2h instead of 23.00 g of monomer of Formula 2a, the polymerization reaction was carried out in the same manner as described in Example 3-1 to obtain 29.90 g of polymer of following Formula 3h(Yield: 81%). From the GPC analysis of the polymer, Mw was 9,428 and PD was 1.79.

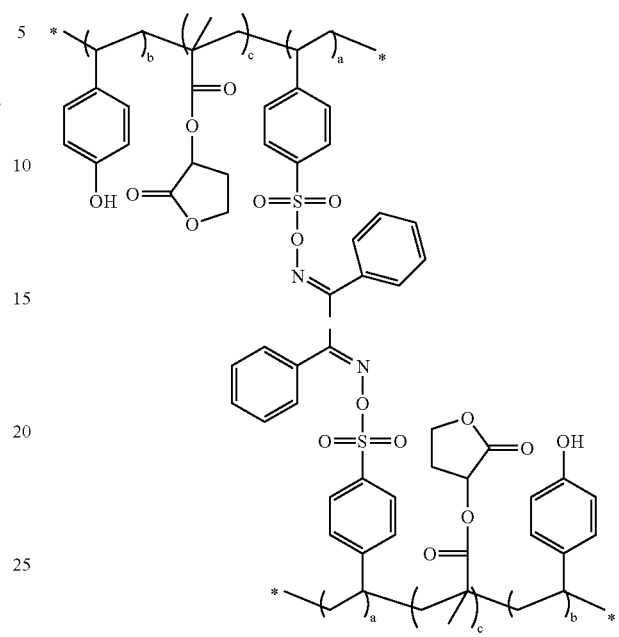

[Formula 3h]

EXAMPLE 3-9

Preparation of Photosensitive Polymer of Formula 3i

Except for using 27.60 g of monomer of Formula 2i instead of 23.00 g of monomer of Formula 2a, the polymerization reaction was carried out in the same manner as described in Example 3-1 to obtain 23.00 g of polymer of following Formula 3i(Yield: 64%). From the GPC analysis of the polymer, Mw was 8,962 and PD was 2.10.

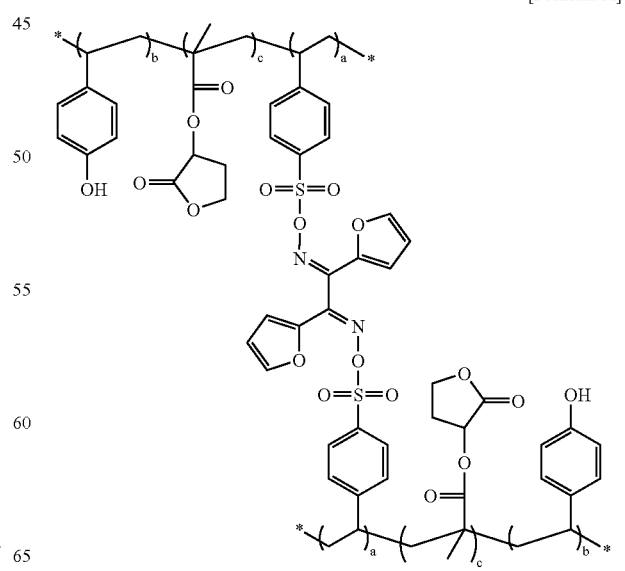

[Formula 3i]

EXAMPLE 3-10

Preparation of Photosensitive Polymer of Formula 3j

Except for using 33.60 g of monomer of Formula 2j instead of 23.00 g of monomer of Formula 2a, the polymerization reaction was carried out in the same manner as described in Example 3-1 to obtain 31.40 g of polymer of following Formula 3j(Yield: 75%). From the GPC analysis of the polymer, Mw was 9,408 and PD was 2.03.

[Formula 3j]

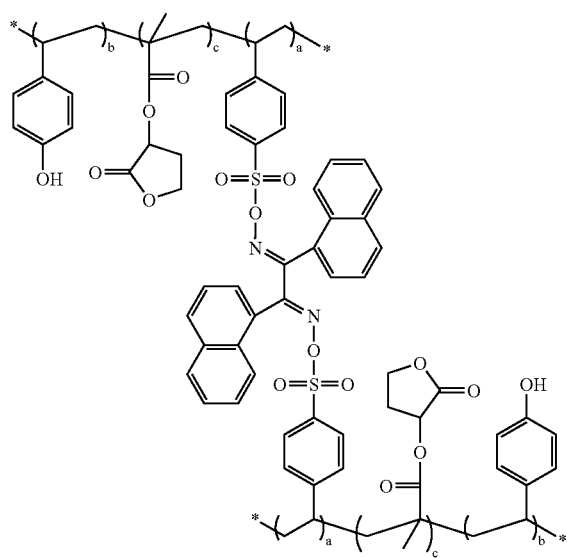

EXAMPLE 3-11

Preparation of Photosensitive Polymer of Formula 3k

Except for using 27.50 g of monomer of Formula 2k instead of 23.00 g of monomer of Formula 2a, the polymerization reaction was carried out in the same manner as described in Example 3-1 to obtain 23.30 g of polymer of following Formula 3k(Yield: 65%). From the GPC analysis of the polymer, Mw was 9,981 and PD was 1.98.

[Formula 3k]

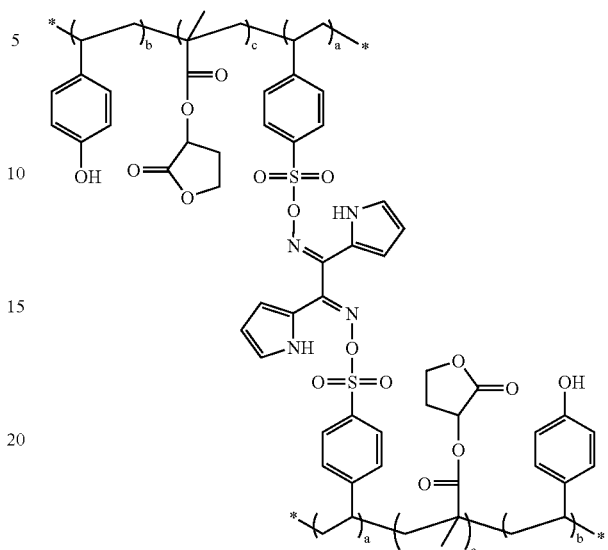

EXAMPLE 3-12

Preparation of Photosensitive Polymer of Formula 3l

Except for using 24.80 g of monomer of Formula 2l instead of 23.00 g of monomer of Formula 2a, the polymerization reaction was carried out in the same manner as described in Example 3-1 to obtain 19.50 g of polymer of following Formula 3l(Yield: 59%). From the GPC analysis of the polymer, Mw was 9,410 and PD was 1.91.

[Formula 3l]

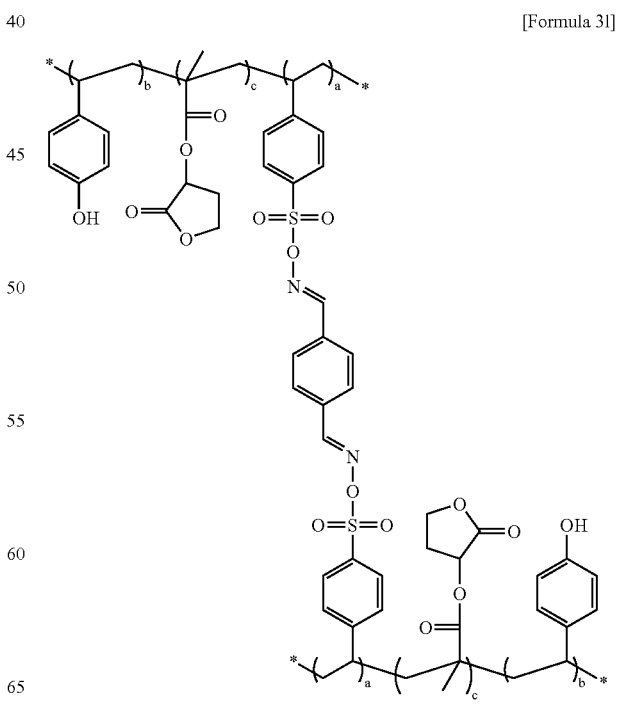

EXAMPLE 3-13

Preparation of Photosensitive Polymer of Formula 3m

Except for using 27.30 g of monomer of Formula 2m instead of 23.00 g of monomer of Formula 2a, the polymerization reaction was carried out in the same manner as described in Example 3-1 to obtain 25.30 g of polymer of following Formula 3m(Yield: 71%). From the GPC analysis of the polymer, Mw was 9,867 and PD was 1.88.

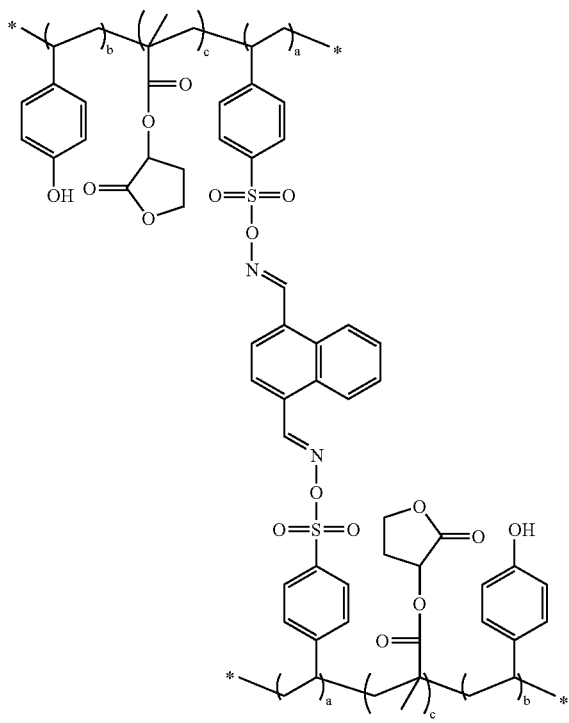

[Formula 3m]

EXAMPLE 3-14

Preparation of Photosensitive Polymer of Formula 3n

Except for using 29.80 g of monomer of Formula 2n instead of 23.00 g of monomer of Formula 2a, the polymerization reaction was carried out in the same manner as described in Example 3-1 to obtain 25.20 g of polymer of following Formula 3n(Yield: 66%). From the GPC analysis of the polymer, Mw was 10,963 and PD was 1.80.

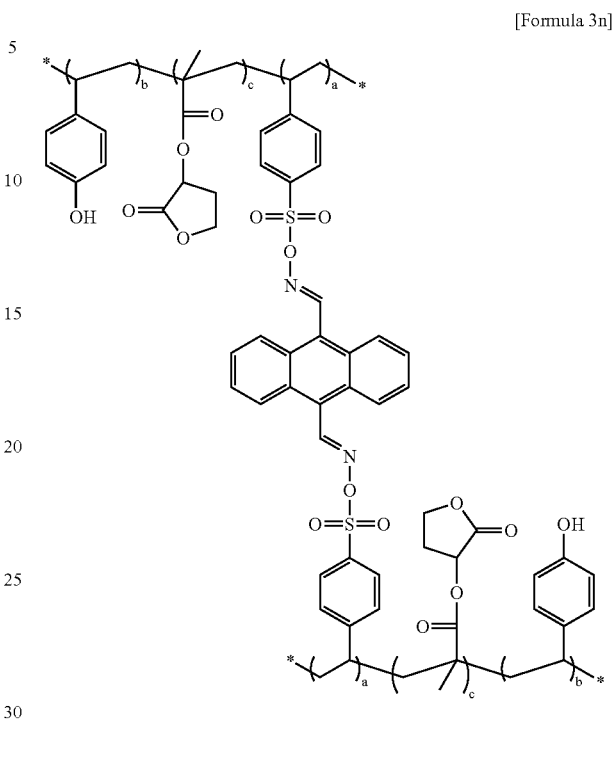

[Formula 3n]

EXAMPLE 4-1

Preparation of Photosensitive Polymer of Formula 4a 300 mL of tetrahydrofuran (THF) was added to a 500 mL 4-neck flask on which a Liebig condenser, a temperature controller and a nitrogen injector were mounted, then nitrogen gas was injected and the reactant was stirred for 30 minutes. 11.50 g of monomer (Formula 2a) prepared in Example 2-1, 5.86 g of 2-methyl-2-adamantyl methacrylate, 4.25 g of gamma-butyrolacto methacrylate, 5.91 g of 1-methacrolyl oxy-3-hydroxy adamantane and 3.14 g of azobis (isobutyronitrile) (AIBN) were added to the reactor and the mixture was stirred for 30 minutes under nitrogen atmosphere at 40° C. Thereafter, the reactor was heated to 70° C. and the polymerization was performed for 24 hours. After the completion of the polymerization, the reactor was cooled to room temperature and the reaction solution was added into 2 L of hexane to obtain a precipitate. The obtained precipitate was filtered, washed with 1 L of hexane for several times and vacuum-dried. The dried polymer was dissolved in THF, and the dissolved solution was added with 1.5 L of diethyl ether to obtain a precipitate. The precipitate was filtered, washed with 1 L of diethyl ether for several times and vacuum-dried for 24 hours to prepare 15.96 g of photosensitive polymer of Formula 4a(Yield: 58%). The molecular weight (Mw) and the polydispersity (PD) of the prepared polymer were measured with GPC (Gel permeation chromatography). From the GPC analysis of the polymer, Mw was 9,869 and PD was 1.90.

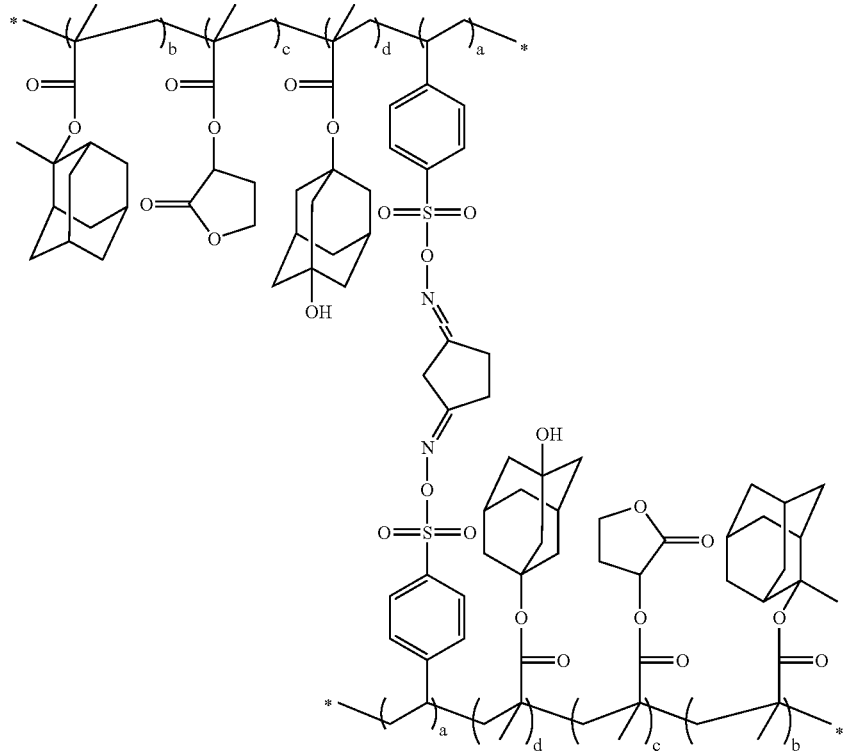
[Formula 4a]
EXAMPLE 4-2
Preparation of Photosensitive Polymer of Formula 4b
Except for using 11.85 g of monomer of Formula 2b instead of 11.50 g of monomer of Formula 2a, the polymerization reaction was carried out in the same manner as described in Example 4-1 to obtain 12.54 g of polymer of following Formula 4b(Yield: 45%). From the GPC analysis of the polymer, Mw was 10,658 and PD was 1.80.
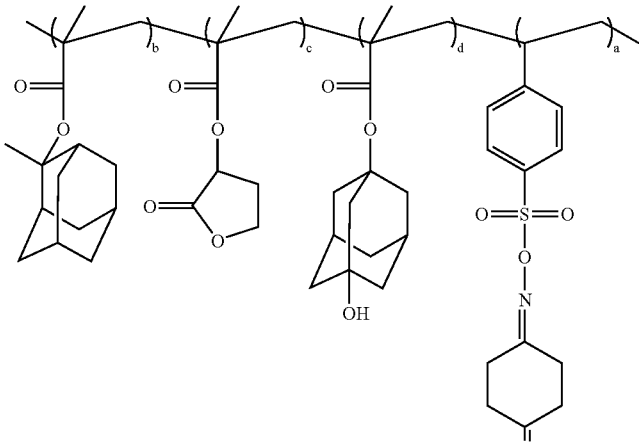
[Formual 4b]

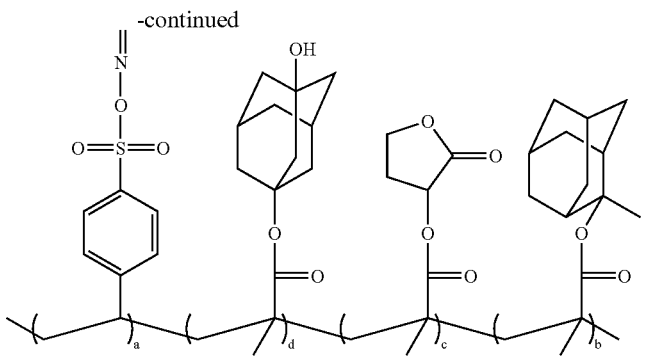

EXAMPLE 4-3

Preparation of Photosensitive Polymer of Formula 4c

Except for using 13.20 g of monomer of Formula 2c instead of 11.50 g of monomer of Formula 2a, the polymerization reaction was carried out in the same manner as described in Example 4-1 to obtain 16.36 g of polymer of following Formula 4c(Yield: 56%). From the GPC analysis of the polymer, Mw was 11,003 and PD was 1.85.

EXAMPLE 4-4

Preparation of Photosensitive Polymer of Formula 4d

Except for using 12.85 g of monomer of Formula 2d instead of 11.50 g of monomer of Formula 2a, the polymerization reaction was carried out in the same manner as described in Example 4-1 to obtain 17.03 g of polymer of following Formula 4d(Yield: 59%). From the GPC analysis of the polymer, Mw was 10,030 and PD was 1.89.

[Formula 4c]

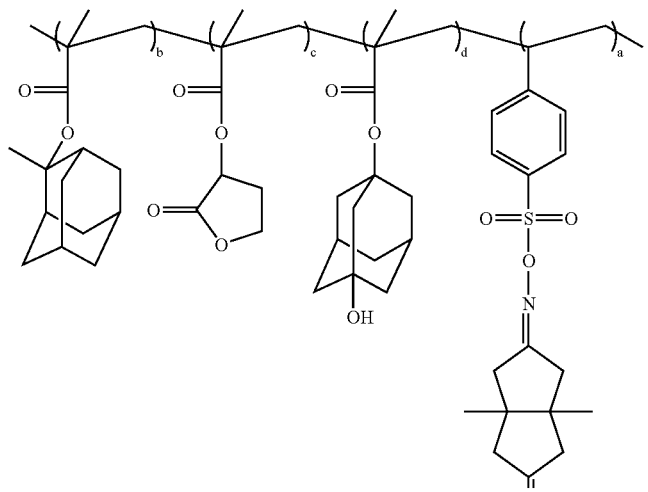

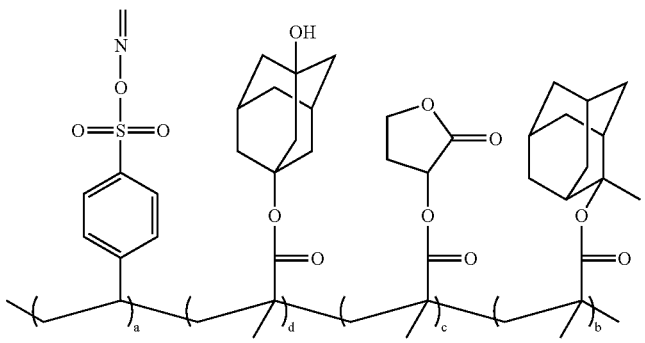

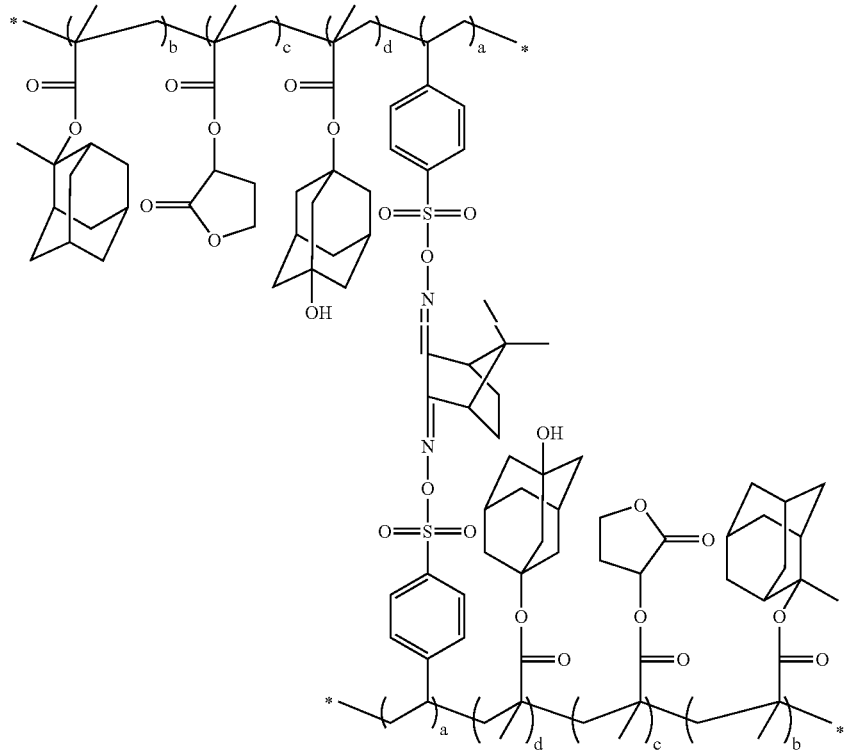
[Formula 4d]
EXAMPLE 4-5
Preparation of Photosensitive Polymer of Formula 4e
Except for using 13.15 g of monomer of Formula 2e instead of 11.50 g of monomer of Formula 2a, the polymerization reaction was carried out in the same manner as described in Example 4-1 to obtain 14.88 g of polymer of following Formula 4e(Yield: 51%). From the GPC analysis of the polymer, Mw was 9,803 and PD was 1.99.
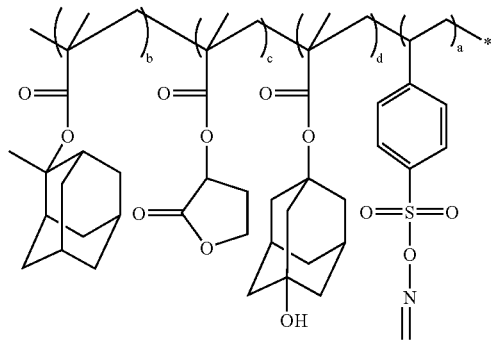
[Formula 4e]

-continued
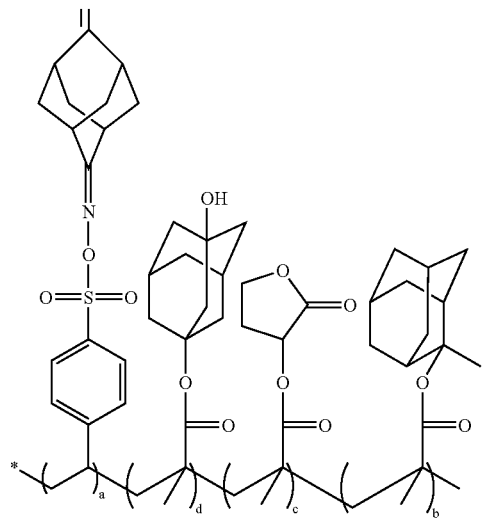
EXAMPLE 4-6
Preparation of Photosensitive Polymer of Formula 4f
Except for using 14.96 g of monomer of Formula 2f instead of 11.50 g of monomer of Formula 2a, the polymerization reaction was carried out in the same manner as described in Example 4-1 to obtain 16.42 g of polymer of following Formula 4f(Yield: 53%). From the GPC analysis of the polymer, Mw was 9,658 and PD was 1.84.
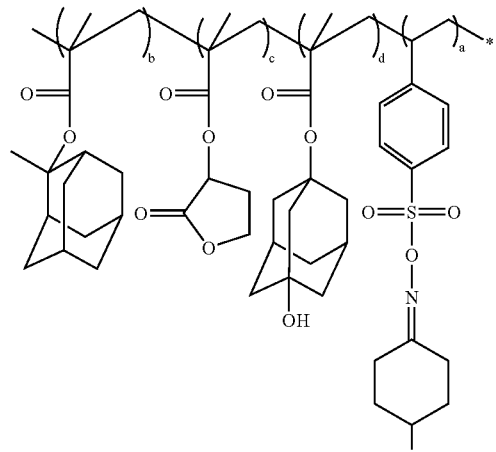
[Formula 4f]

-continued
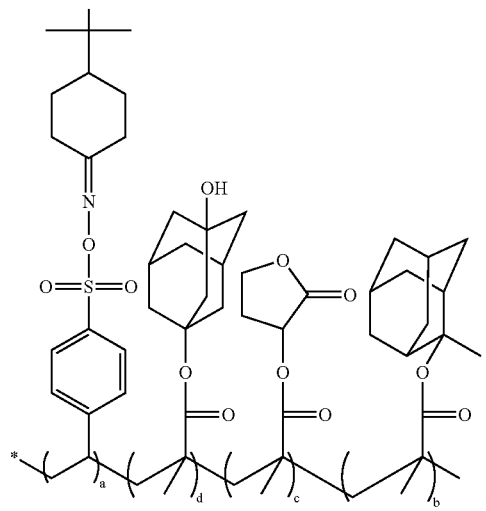
EXAMPLE 4-7
Preparation of Photosensitive Polymer of Formula 4g
Except for using 13.90 g of monomer of Formula 2g instead of 11.50 g of monomer of Formula 2a, the polymerization reaction was carried out in the same manner as described in Example 4-1 to obtain 17.06 g of polymer of following Formula 4g(Yield: 57%). From the GPC analysis of the polymer, Mw was 10,128 and PD was 1.98.
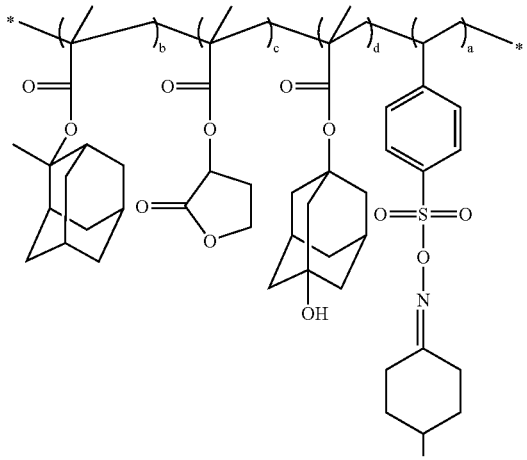
[Formula 4g]

-continued

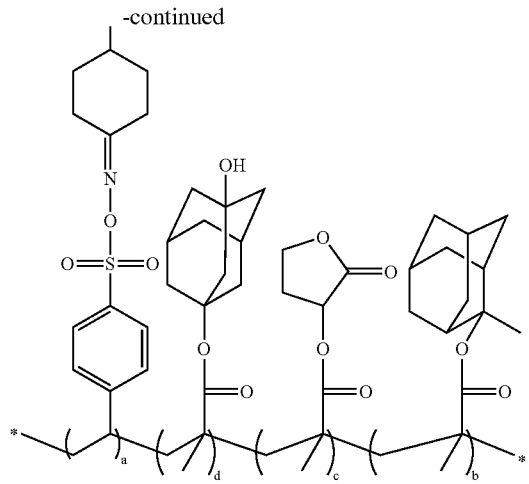

EXAMPLE 4-8

Preparation of Photosensitive Polymer of Formula 4h

Except for using 14.30 g of monomer of Formula 2h instead of 11.50 g of monomer of Formula 2a, the polymerization reaction was carried out in the same manner as described in Example 4-1 to obtain 13.64 g of polymer of following Formula 4h(Yield: 45%). From the GPC analysis of the polymer, Mw was 9,832 and PD was 2.01.

EXAMPLE 4-9

Preparation of Photosensitive Polymer of Formula 4i

Except for using 13.80 g of monomer of Formula 2i instead of 11.50 g of monomer of Formula 2a, the polymerization reaction was carried out in the same manner as described in Example 4-1 to obtain 18.19 g of polymer of following Formula 4i(Yield: 61%). From the GPC analysis of the polymer, Mw was 9,468 and PD was 1.78.

[Formula 4h]

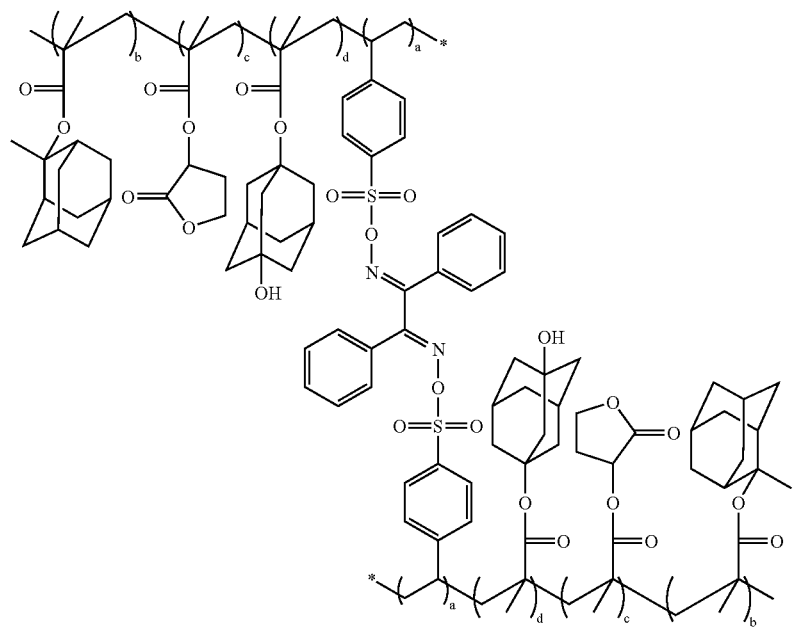

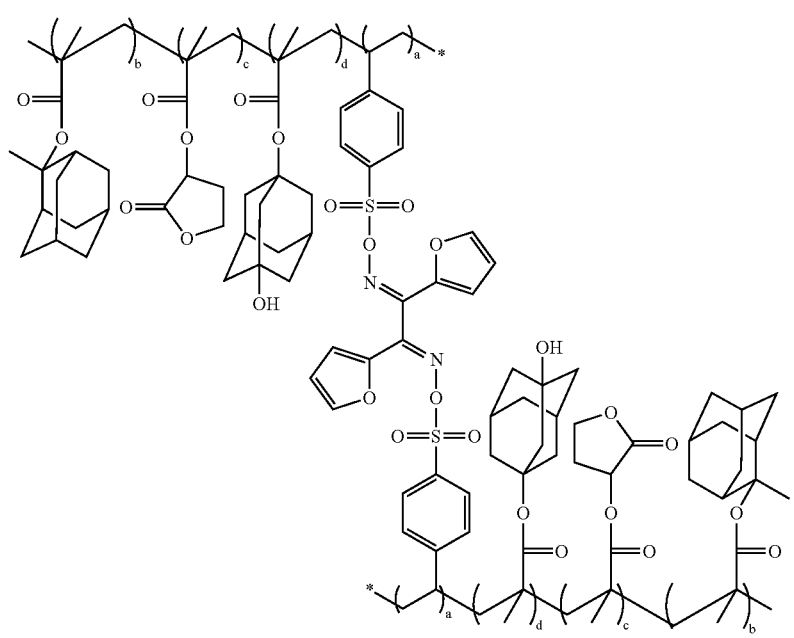

[Formula 4i]

EXAMPLE 4-10

Preparation of Photosensitive Polymer of Formula 4j

Except for using 16.80 g of monomer of Formula 2j instead of 11.50 g of monomer of Formula 2a, the polymerization reaction was carried out in the same manner as described in Example 4-1 to obtain 17.72 g of polymer of following Formula 4j(Yield: 54%). From the GPC analysis of the polymer, Mw was 8,671 and PD was 1.75.

EXAMPLE 4-11

Preparation of Photosensitive Polymer of Formula 4k

Except for using 13.75 g of monomer of Formula 2k instead of 11.50 g of monomer of Formula 2a, the polymerization reaction was carried out in the same manner as described in Example 4-1 to obtain 15.78 g of polymer of following Formula 4k(Yield: 53%). From the GPC analysis of the polymer, Mw was 11,031 and PD was 1.94.

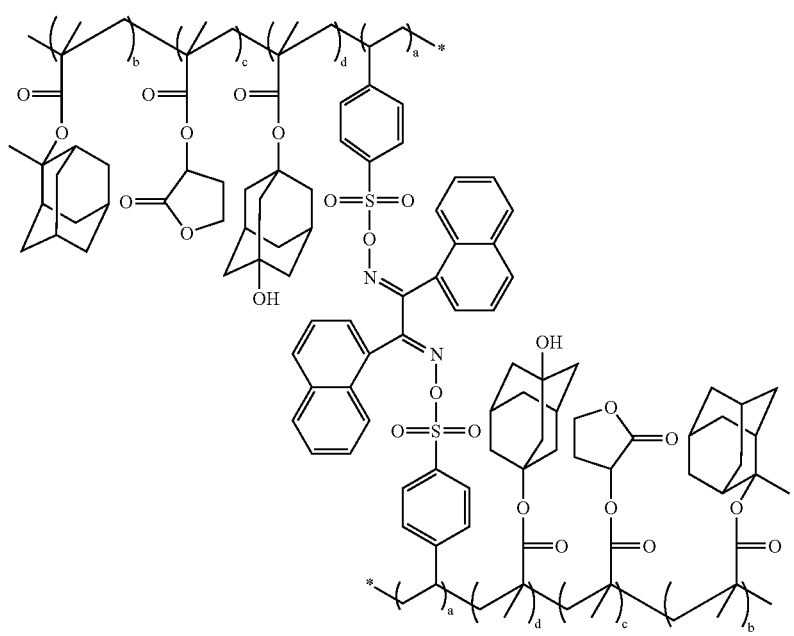

[Formula 4j]

[Formula 4k]
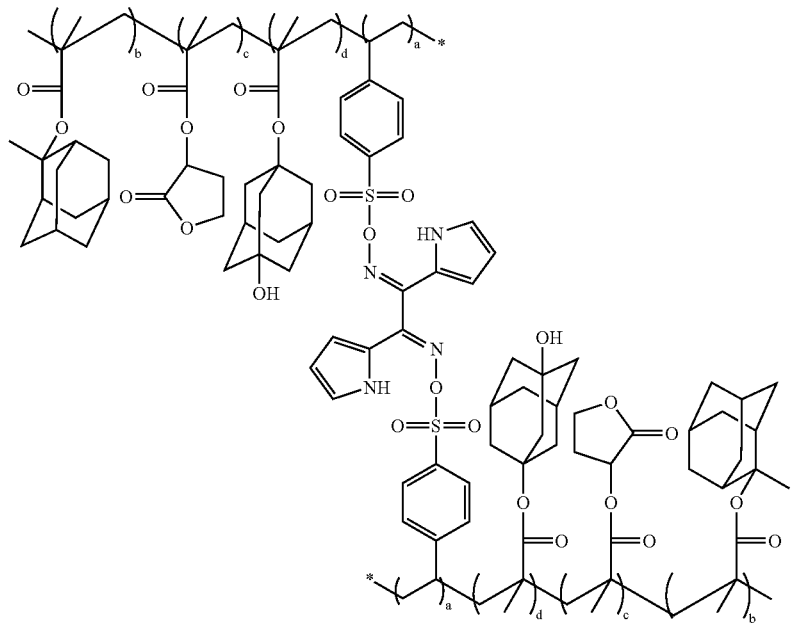
EXAMPLE 4-12
Preparation of Photosensitive Polymer of Formula 4l
Except for using 12.40 g of monomer of Formula 2l instead of 11.50 g of monomer of Formula 2a, the polymerization reaction was carried out in the same manner as described in Example 4-1 to obtain 16.77 g of polymer of following Formula 4l(Yield: 59%). From the GPC analysis of the polymer, Mw was 10,091 and PD was 1.95.
[Formula 4l]
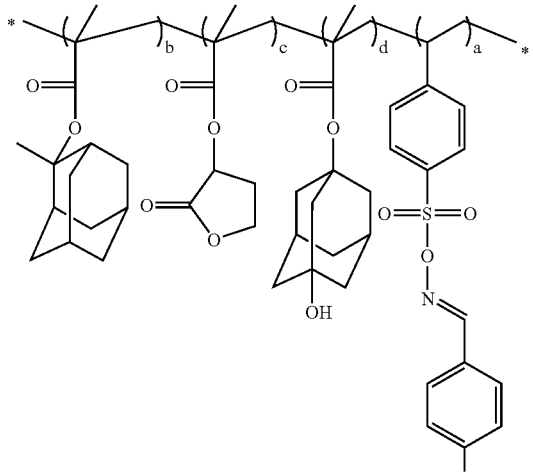

-continued

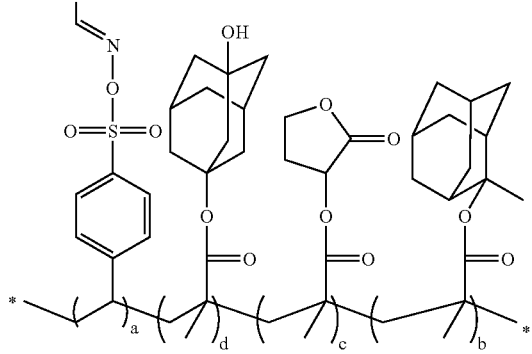

EXAMPLE 4-13

Preparation of Photosensitive Polymer of Formula 4m

Except for using 13.65 g of monomer of Formula 2m instead of 11.50 g of monomer of Formula 2a, the polymerization reaction was carried out in the same manner as described in Example 4-1 to obtain 16.02 g of polymer of following Formula 4m(Yield: 54%). From the GPC analysis of the polymer, Mw was 9,145 and PD was 1.89.

EXAMPLE 4-14

Preparation of Photosensitive Polymer of Formula 4n

Except for using 14.90 g of monomer of by Formula 2n instead of 11.50 g of monomer of Formula 2a, the polymerization reaction was carried out in the same manner as described in Example 4-1 to obtain 15.77 g of polymer of following Formula 4n(Yield: 51%). From the GPC analysis of the polymer, Mw was 9,768 and PD was 2.20.

[Formula 4m]

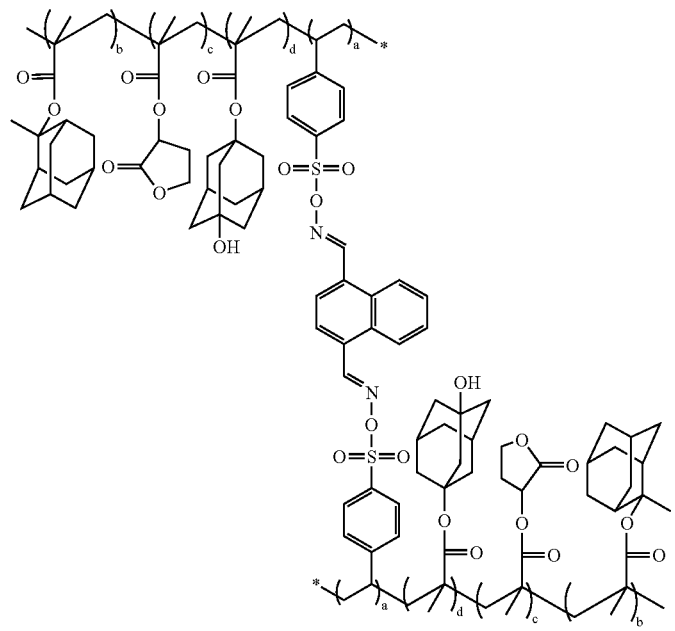

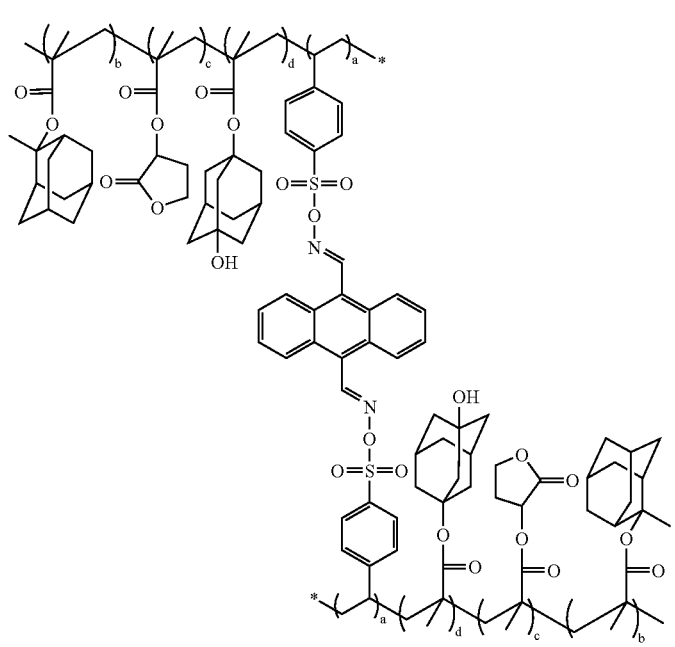

[Formula 4n]

EXAMPLES 5-1 THROUGH 5-14

Preparation of Photoresist Composition Containing Photosensitive Polymer Prepared in Examples 3-1~3-14

2.5 g of the photosensitive polymer (Formula 3a through Formula 3n) prepared in one among Example 3-1 through Example 3-14, 0.08 g of triphenylsulfonium triflate and 0.03 g of triethanolamine were dissolved in 30 g of propyleneglycol monomethylether acetate (PGMEA). Then the dissolved mixture was filtered with 0.20 μm filter to prepare the photoresist composition.

EXAMPLES 6-1 THROUGH 6-14

Preparation of Photoresist Composition Containing Photosensitive Polymer Prepared in Examples 4-1~4-14

2.5 g of the photosensitive polymer (Formula 4a through Formula 4n) prepared in one among Example 4-1 through Example 4-14, 0.08 g of triphenylsulfonium triflate and 0.03 g of triethanolamine were dissolved in 30 g of propyleneglycol monomethylether acetate (PGMEA). Then the dissolved mixture was filtered with 0.20 μm filter to prepare the photoresist composition.

COMPARATIVE EXAMPLE 1

Preparation of Photoresist Composition Containing Photosensitive Polymer of Formula 7

Except for using 3.58 g of t-butyl methacrylate instead of 4.25 g of gamma-butyrolacto methacrylate and 23.00 g of monomer of Formula 2a, the polymerization reaction was carried out in the same manner as described in Example 3-1 to obtain the polymer of Formula 7. In the polymer of Formula 7, the amounts (mole %) of the two repeating units are 50 mole % and 50 mole %, respectively. From the GPC analysis of the polymer, Mw was 14,700 and PD was 2.22.

Next, 2.5 g of prepared photosensitive polymer of Formula 7, 0.08 g of triphenylsulfonium triflate and 0.03 g of triethanolamine were dissolved in 30 g of propyleneglycol monomethyletheracetate (PGMEA), and filtered with 0.20 μm filter to prepare the photoresist composition.

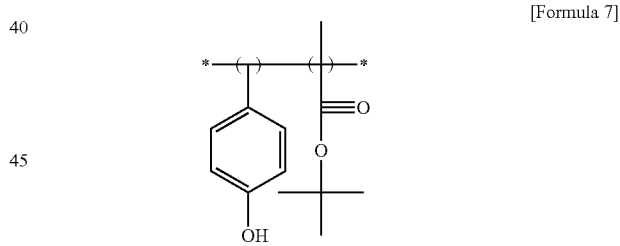

[Formula 7]

COMPARATIVE EXAMPLE 2

Preparation of Photoresist Composition Containing Photosensitive Polymer of Formula 8

Except for not using 11.50 g of monomer of Formula 2a, the polymerization reaction was carried out in the same manner as described in Example 4-1 to obtain the polymer of Formula 8. In the polymer of Formula 8, the amounts (mole %) of the three repeating units are 50 mole %, 25 mole %, and 25 mole %, respectively From the GPC analysis of the polymer, Mw was 10,100 and PD was 1.89.

Next, 2.5 g of prepared photosensitive polymer of Formula 8, 0.08 g of triphenylsulfonium triflate and 0.03 g of triethanolamine were dissolved in 30 g of propyleneglycol monomethyletheracetate (PGMEA), and filtered with 0.20 μm filter to prepare the photoresist composition.

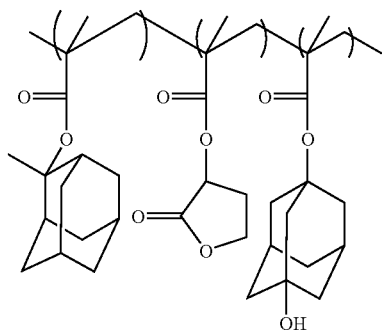

[Formula 8]

EXAMPLE 7

Formation of Photoresist Pattern Using the Photoresist Composition

The photoresist composition prepared in Examples 5-1~5-14, Examples 6-1~6-14, and Comparative examples 1~2 was spin-coated to a thickness of 0.1 μm on a silicon wafer, which was treated with hexamethyldisilazane (HMDS), to form a photoresist thin-layer. The photoresist layer was pre-baked at a temperature of 100° C. (or 120° C.) for 90 seconds in an oven or on a hot plate, and was optimum exposed with an ArF excimer laser having 0.6 of aperture number or an KrF excimer laser having 0.5 of aperture number. Next the photoresist layer was post-baked at a temperature of 100° C. (or 120° C.) for 90 seconds. Thereafter, the baked wafer was developed with 2.38 weight % of TMAH solution for about 30 seconds, thereby forming a 0.20 μm or 0.15 μm line/space patterns. The line width variations of the produced photoresist patterns were shown in Table 1

TABLE 1

| Photoresist composition | Resolution (nm) | | Line width variation (nm) |
| --- | --- | --- | --- |
| | KrF excimer laser | ArF excimer laser | |
| Example 5-1 | 200 | | 3.1 |
| Example 5-2 | 200 | | 3.2 |
| Example 5-3 | 200 | | 2.4 |
| Example 5-4 | 200 | | 3.5 |
| Example 5-5 | 200 | | 3.1 |
| Example 5-6 | 200 | | 3.1 |
| Example 5-7 | 200 | | 2.8 |
| Example 5-8 | 200 | | 2.8 |
| Example 5-9 | 200 | | 2.6 |
| Example 5-10 | 200 | | 2.9 |
| Example 5-11 | 200 | | 3.4 |
| Example 5-12 | 200 | | 3.6 |
| Example 5-13 | 200 | | 3.2 |
| Example 5-14 | 200 | | 3.0 |
| Example 6-1 | | 150 | 2.1 |
| Example 6-2 | | 150 | 2.0 |
| Example 6-3 | | 150 | 2.3 |
| Example 6-4 | | 150 | 2.3 |
| Example 6-5 | | 150 | 2.6 |
| Example 6-6 | | 150 | 2.1 |
| Example 6-7 | | 150 | 1.9 |
| Example 6-8 | | 150 | 1.8 |
| Example 6-9 | | 150 | 3.0 |
| Example 6-10 | | 150 | 3.1 |
| Example 6-11 | | 150 | 2.5 |
| Example 6-12 | | 150 | 2.4 |
| Example 6-13 | | 150 | 2.2 |
| Example 6-14 | | 150 | 2.2 |
| Comparative example 1 | 200 | | 4.3 |
| Comparative example 2 | | 150 | 3.2 |

As shown Table 1, the photoresist composition containing photosensitive polymer of the present invention has superior line width stability compared to the photoresist composition containing conventional chemically amplified photosensitive polymer (Formula 7 and Formula 8). Also, the photoresist layers, which were prepared with the photoresist composition of Examples 5-1~5-14 and Examples 6-1~6-14, were exposed with EUV exposure apparatus, which results in successful formations of 50 nm line/space patterns.

As described above, the main chain of the polymer according to the present invention is decomposed by ultraviolet rays as well as an acid. Thus, the resolution of the photoresist pattern and process margin can be improved, and a fine pattern can be formed due to the high dry etching stability and a stable PEB(Post Exposure Baking) temperature sensitivity. In addition, the photoresist polymer and the photoresist composition containing the same of the present invention can improve the focus depth margin and the line edge roughness of the photoresist pattern.

The invention claimed is:

1. A photoresist monomer represented by following Formula 1

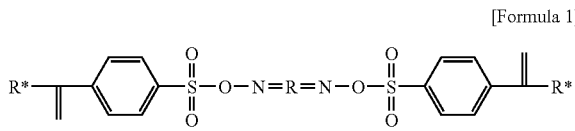

[Formula 1]

In Formula 1, R* is independently a hydrogen or a methyl group, and R is a substituted or unsubstituted $C_1$~$C_{25}$ alkyl group with or without an ether group, or a substituted or unsubstituted $C_4$~$C_{25}$ hydrocarbon group including an aryl group, a heteroaryl group, a cycloalkyl group or a multicycloalkyl group with or without an ether group, a ketone group or a sulfur.

2. The photoresist monomer of claim 1, wherein R is selected from the group consisting of

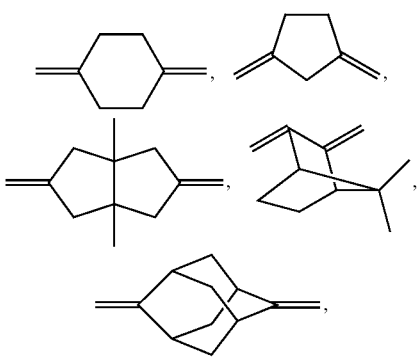

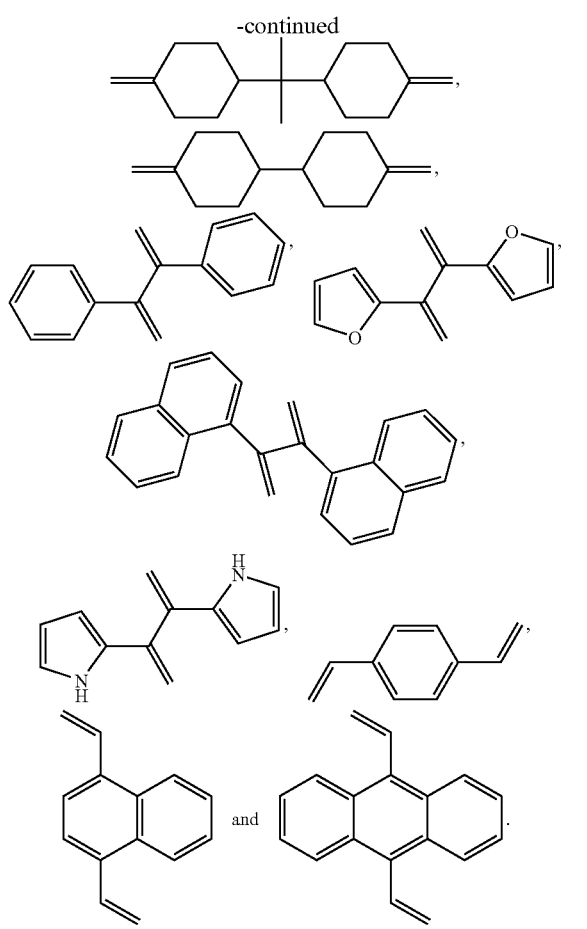

3. A photoresist polymer containing a repeating unit represented by following Formula 2

[Formula 2]

In Formula 2, R* is independently a hydrogen or a methyl group, and R is a substituted or unsubstituted $C_1 \sim C_{25}$ alkyl group with or without an ether group, or a substituted or unsubstituted $C_4 \sim C_{25}$ hydrocarbon group including an aryl group, a heteroaryl group, a cycloalkyl group or a multicycloalkyl group with or without an ether group, a ketone group or a sulfur.

4. The photoresist polymer of claim 3, wherein the photoresist polymer is represented by following Formula 3

[Formula 3]

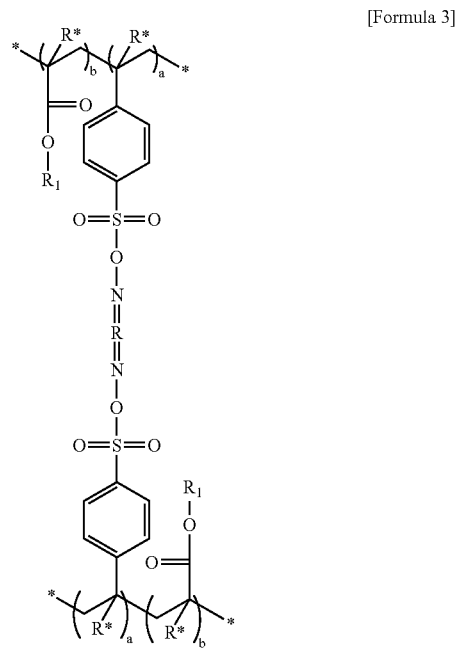

In Formula 3, R* and R are as defined in Formula 2, $R_1$ independently is a $C_1 \sim C_{25}$ alkyl group or cycloalkyl group with or without an ether group or an ester group, and a and b

[Formula 1]

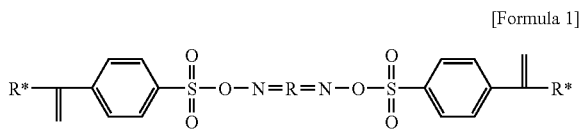

In Formula 1, R* is independently a hydrogen or a methyl group, and R is a substituted or unsubstituted $C_1 \sim C_{25}$ alkyl group with or without an ether group, or a substituted or unsubstituted $C_4 \sim C_{25}$ hydrocarbon group including an aryl group, a heteroaryl group, a cycloalkyl or a multicycloalkyl group with or without an ether group, a ketone group or a sulfur, independently represent mole % of repeating units constituting the upper polymer chain and the lower polymer chain of the polymer, and are 1~99 mole % and 1~99 mole %, respectively.

5. The photoresist polymer of claim 3, wherein the photoresist polymer is represented by following Formula 4

[Formula 4]

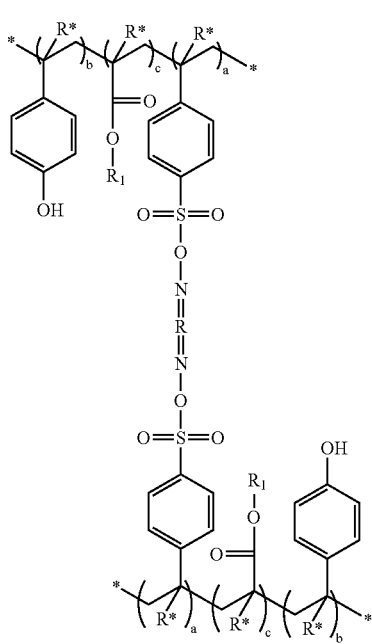

In Formula 4, R* and R are as defined in Formula 2, $R_1$ independently is a $C_1$~$C_{25}$ alkyl group or cycloalkyl group with or without an ether group or an ester group, and a, b and c independently represent mole % of repeating units constituting the upper polymer chain and the lower polymer chain of the polymer, and are 1~98 mole %, 1~98 mole % and 1~98 mole %, respectively.

6. The photoresist polymer of claim 3, wherein the photoresist polymer is represented by following Formula 5

[Formula 5]

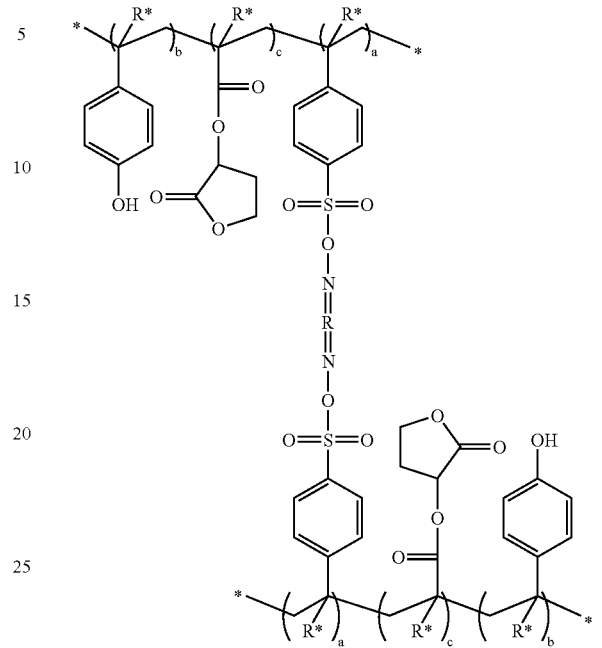

In Formula 5, R* and R are as defined in Formula 2, and a, b and c independently represent mole % of repeating units constituting the upper polymer chain and the lower polymer chain of the polymer, and are 1~98 mole %, 1~98 mole % and 1~98 mole %, respectively.

7. The photoresist polymer of claim 3, wherein the photoresist polymer is represented by following Formula 6

[Formula 6]

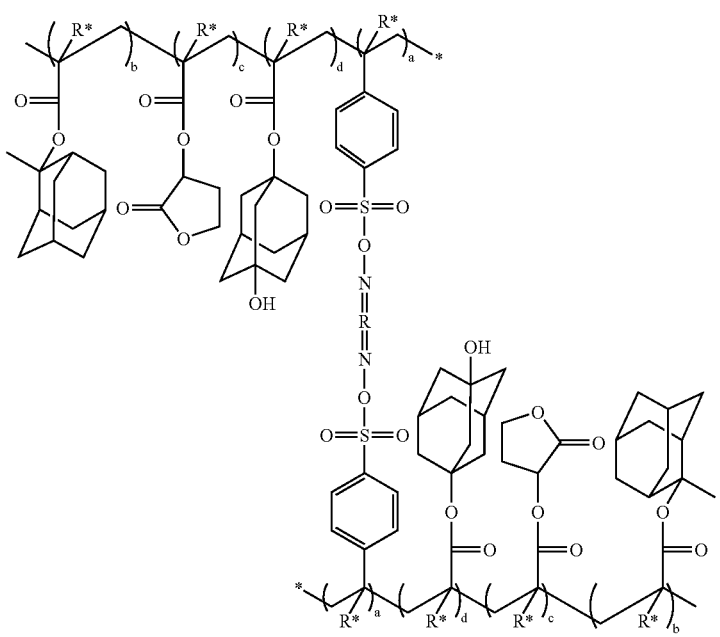

In Formula 6, R* and Rare as defined in Formula 2, and a, b, c and d independently represent mole % of repeating units constituting the upper polymer chain and the lower polymer chain of the polymer, and are 1~97 mole %, 1~97 mole %, 1~97 mole % and 1~97 mole %, respectively.

8. A photoresist composition comprising:
a polymer containing monomer represented by following Formula 1;
a photo-acid generator for generating an acid: and
an organic solvent,
wherein the amount of the photo-acid generator is 0.1 to 20 weight parts with respect to the 100 weight parts of the photoresist polymer, and the amount of the organic solvent is 300 to 5000 weight parts with respect to 100 weight parts of the photoresist polymer,

[Formula 1]

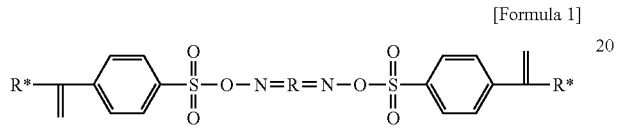

In Formula 1, R* is independently a hydrogen or a methyl group, and R is a substituted or unsubstituted $C_1$~$C_{25}$ alkyl group with or without an ether group, or a substituted or unsubstituted $C_4$~$C_{25}$ hydrocarbon group including an aryl group, a heteroaryl group, a cycloalkyl or a multicycloalkyl group with or without an ether group, a ketone group or a sulfur.

9. A method for forming a photoresist pattern, comprising the steps of:
   a) coating a photoresist composition on a substrate to form a photoresist layer;
   b) exposing the photoresist layer to a light of a predetermined pattern;
   c) heating the exposed photoresist layer; and
   d) developing the heated photoresist layer to form the photoresist pattern,
   wherein the photoresist composition comprises a photoresist polymer containing monomer represented by following Formula 1, a photo-acid generator for generating an acid, and an organic solvent.

* * * * *